(12) United States Patent
Schultz et al.

(10) Patent No.: US 8,809,015 B2
(45) Date of Patent: Aug. 19, 2014

(54) METHODS AND SYSTEMS FOR THE PRODUCTION OF HYDROCARBON PRODUCTS

(75) Inventors: Michael Anthony Schultz, Roselle, IL (US); James Obern, Roselle, IL (US); Sean Dennis Simpson, Auckland (NZ)

(73) Assignee: LanzaTech New Zealand Limited, Auckland (NZ)

( * ) Notice: Subject to any disclaimer, the term of this patent is extended or adjusted under 35 U.S.C. 154(b) by 0 days.

(21) Appl. No.: 13/579,071

(22) PCT Filed: Oct. 21, 2011

(86) PCT No.: PCT/US2011/057208
§ 371 (c)(1),
(2), (4) Date: Aug. 15, 2012

(87) PCT Pub. No.: WO2012/054798
PCT Pub. Date: Apr. 26, 2012

(65) Prior Publication Data
US 2013/0210096 A1 Aug. 15, 2013

Related U.S. Application Data

(60) Provisional application No. 61/405,854, filed on Oct. 22, 2010, provisional application No. 61/408,236, filed on Oct. 29, 2010, provisional application No. 61/439,316, filed on Feb. 3, 2011.

(30) Foreign Application Priority Data

Dec. 3, 2010 (NZ) ........................ 589700

(51) Int. Cl.
| | | |
|---|---|---|
| C12P 1/00 | (2006.01) | |
| C12P 7/54 | (2006.01) | |
| C12P 7/18 | (2006.01) | |
| C10G 11/18 | (2006.01) | |
| C10K 3/02 | (2006.01) | |
| C12P 5/02 | (2006.01) | |
| C12P 7/06 | (2006.01) | |
| C12M 1/107 | (2006.01) | |
| C12M 1/00 | (2006.01) | |
| C01B 3/38 | (2006.01) | |
| C10G 9/36 | (2006.01) | |

(52) U.S. Cl.
CPC ............ *C12P 7/54* (2013.01); *C10J 2300/1846* (2013.01); *C10J 2300/1681* (2013.01); *C12P 7/18* (2013.01); *C01B 2203/0283* (2013.01); *C10G 2300/708* (2013.01); *C01B 2203/06* (2013.01); *C01B 2203/061* (2013.01); *Y02E 50/343* (2013.01); *C10G 11/18* (2013.01); *C01B 2203/0233* (2013.01); *C10K 3/026* (2013.01); *C12P 5/02* (2013.01); *C12P 7/065* (2013.01); *C10J 2300/0943* (2013.01); *C01B 2203/1058* (2013.01); *C12M 21/04* (2013.01); *C12M 43/00* (2013.01); *C12P 7/06* (2013.01); *C01B 3/38* (2013.01); *C10G 9/36* (2013.01); *C10G 2300/1011* (2013.01); *Y02E 50/17* (2013.01); *C01B 2203/043* (2013.01)
USPC ............. 435/41; 435/140; 435/160; 435/161; 435/163; 435/135; 435/157

(58) Field of Classification Search
USPC ............ 435/41, 135, 157, 160, 140, 161, 163
See application file for complete search history.

(56) References Cited

U.S. PATENT DOCUMENTS

| | | |
|---|---|---|
| 5,173,429 A | 12/1992 | Gaddy et al. |
| 5,593,886 A | 1/1997 | Gaddy et al. |
| 5,807,722 A | 9/1998 | Gaddy |
| 5,821,111 A | 10/1998 | Gaddy et al. |
| 6,136,577 A | 10/2000 | Gaddy |
| 6,340,581 B1 | 1/2002 | Gaddy |
| 6,368,819 B1 | 4/2002 | Gaddy et al. |
| 6,753,170 B2 | 6/2004 | Gaddy et al. |
| 2005/0112056 A1 | 5/2005 | Hampden-Smith et al. |
| 2007/0275447 A1 | 11/2007 | Lewis et al. |
| 2009/0031615 A1 | 2/2009 | Joshi et al. |

FOREIGN PATENT DOCUMENTS

| | | |
|---|---|---|
| NZ | WO2007/115157 | 10/2007 |
| NZ | WO2008/115080 | 9/2008 |
| NZ | WO2009/064200 | 5/2009 |
| NZ | WO2009/113878 | 9/2009 |
| NZ | WO2009/151342 | 12/2009 |
| WO | WO 02/08438 | 1/2002 |
| WO | WO 2009058028 A1 * | 5/2009 |

OTHER PUBLICATIONS

Gary and Handwerk (2001). Petroleum Refining: Technology and Economics (4th ed.). CRC Press.

Demler, M., Weuster-Botz, "Reaction Engineering Analysis of Hydrogenotrophic Production of Acetic Acid by Acetobacterum Woodii", Biotechnology and Bioengineering, vol. 108, No. 2, Feb. 2011.

(Continued)

*Primary Examiner* — Susan Hanley
*Assistant Examiner* — Nghi Nguyen
(74) *Attorney, Agent, or Firm* — Frank S. Molinaro

(57) ABSTRACT

Methods and systems for the production of hydrocarbon products, including providing a substrate comprising CO to a bioreactor containing a culture of one or more micro-organisms; and fermenting the culture in the bioreactor to produce one or more hydrocarbon products. The substrate comprising CO is derived from an industrial process selected from the group comprising steam reforming processes, refinery processes, steam cracking processes, and reverse water gas shift processes.

11 Claims, 6 Drawing Sheets

(56) References Cited

OTHER PUBLICATIONS

Svetlichny, V.A., Sokolova, T.G. et al (1991), Systematic and Applied Microbiology 14: 254-260.
Simpa et. al. Critical Reviews in Biotechnology, 2006 vol. 26. pp. 41-65.
Hensirisak et. al. Scale-up of microbubble dispersion generator for aerobic fermentation; Applied Biochemistry and Biotechnology vol. 101, No. 3 / Oct. 2002.
K. T. Klasson, et al. (1991). Bioreactors for synthesis gas fermentations resources. Conservation and Recycling, 5; 145-165.
K. T. Klasson, et al. (1991). Bioreactor design for synthesis gas fermentations. Fuel. 70. 605-614.
K. T. Klasson, et al. (1992). Bioconversion of synthesis gas into liquid or gaseous fuels. Enzyme and Microbial Technology. 14; 602-608.
J. L. Vega, et al. (1989). Study of Gaseous Substrate Fermentation: Carbon Monoxide Conversion to Acetate. 2. Continuous Culture. Biotechnology and Bioengineering. 34. 6. 785-793.
J. L. Vega, et al. (1989). Study of gaseous substrate fermentations: Carbon monoxide conversion to acetate. 1. Batch culture. Biotechnology and Bioengineering. 34. 6. 774-784.
J. L. Vega, et al. (1990). Design of Bioreactors for Coal Synthesis Gas Fermentations. Resources, Conservation and Recycling. 3. 149-160.
Raju et al, Fuel Processing Technology, doi: 10.1016/j.fuproc.2008.09.011, 2008.

* cited by examiner

METHODS AND SYSTEMS FOR THE PRODUCTION OF HYDROCARBON PRODUCTS

CROSS REFERENCE TO RELATED APPLICATIONS

This application is a National Stage of International Application No. PCT/US2011/057208 filed on Oct. 21, 2011, which claims the priority of U.S. Provisional Application No. 61/405,854 filed on Oct. 22, 2010; U.S. Provisional Application No. 61/408,236 filed on Oct. 29, 2010; U.S. Provisional 61/439,316 filed on Feb. 3, 2011; and New Zealand Patent Application No. 589700 filed on Dec. 3, 2010. The contents of the above referenced applications are incorporated herein in their entirety.

FIELD OF THE INVENTION

This invention relates generally to methods for producing products, particularly alcohols, by microbial fermentation. In particular, the invention relates to methods for producing fermentation products from industrial gases associated with steam reforming.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to continue to grow sharply in future, due to an increased interest in ethanol in Europe, Japan, the USA and several developing nations.

For example, in the USA, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, and the cultivation of starch or sucrose-producing crops for ethanol production is not economically sustainable in all geographies. Therefore, it is of interest to develop technologies to convert lower cost and/or more abundant carbon resources into fuel ethanol.

CO is a major, free, energy-rich by-product of the incomplete combustion of organic materials such as coal or oil and oil derived products. For example, the steel industry in Australia is reported to produce and release into the atmosphere over 500,000 tonnes of CO annually.

Catalytic processes may be used to convert gases consisting primarily of CO and/or CO and hydrogen ($H_2$) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

Although processes for the fermentation of substrates containing CO and $H_2$ by microorganisms are known, the potential for scaling and integrating these processes into an industrial context has barely been explored. Petrochemical plants and oil refineries produce large quantities of CO as by-products and the potential exists to use this "waste" gas to produce valuable products. Additionally, a significant proportion of the waste gases are currently sent to flare (burned), or alternatively used as a source of fuel, both of which produce the undesirable greenhouse gas $CO_2$. Accordingly, there exists the potential to make improvements to industrial processes by exploiting the waste gases and energy produced thereby for use in fermentation to produce desirable products while simultaneously reducing gaseous carbon emissions from industrial plants.

Hydrogen is predicted to become a major feedstock for use in hydrogen fuel cells which are being developed for use in technology ranging from cars to consumer electronics. Further, it may be used as a combustible fuel. Hydrogen is also required in refineries for a large number of hydrotreating and hydrocracking processes, to remove sulphur, nitrogen and other impurities from hydrotreater feed and to hydrocrack heavier gas oils to distillates. As hydrogen production is capital intensive, it is desirable to develop methods that increase hydrogen production and recovery efficiency, especially from low-purity streams. In the absence of hydrogen recovery, such streams end up in fuel gas or sent to flare and the high-value hydrogen component is effectively wasted.

It is an object of the present invention to provide a process that overcomes or ameliorates at least one of the disadvantages of the prior art, or at least to provide the public with a useful choice.

SUMMARY OF THE INVENTION

According to a first broad aspect, the invention provides a method of producing at least one hydrocarbon product, the method including:
i) providing a substrate comprising CO and/or $H_2$ to a bioreactor containing a culture of one or more micro-organisms; and ii) fermenting the culture in the bioreactor to produce one or more hydrocarbon products, wherein the substrate of step (i) is derived from an industrial process selected from the group comprising steam reforming processes; refinery processes; steam cracking processes and reverse water gas shift processes.

In preferred embodiments, the one or more hydrocarbon products is one or more alcohols. In one embodiment the one or more hydrocarbon products is ethanol. In an alternative embodiment the one or more hydrocarbon products is 2,3-butanediol. In certain embodiments the one or more hydrocarbon products is ethanol and 2,3-butanediol.

According to a second aspect, the invention provides a method of producing a hydrocarbon product, the method including:
 i) providing a substrate comprising CO and/or $H_2$ to a bioreactor containing a culture of one or more microorganisms;
 ii) fermenting the culture in the bioreactor to produce one or more hydrocarbon products;
wherein the substrate comprising CO and/or $H_2$ is received from a step of the steam reforming process, the process including at least one of;
 i) a steam reforming (SR) step being defined generally by the equation: $CH_4+H_2O \rightarrow CO+3H_2$; and/or
 ii) a water-gas shift (WGS) step being defined generally by the equation: $CO+H_2O \rightarrow H_2+CO_2$.

Preferably, the substrate comprising CO and/or $H_2$ is received directly from the steam reforming step.

In one embodiment, there is provided a method of producing a hydrocarbon product, the method including pre-forming comprising at least one of:
 i) a steam reforming step, the step being defined generally by the equation: $CH_4+H_2O \rightarrow CO+3H_2$; and/or
 ii) a water-gas shift step being defined generally by the equation: $CO+H_2O \rightarrow H_2+CO_2$
wherein said pre-forming is for treating and/or providing a substrate comprising CO and/or $H_2$ for a bioreactor.

In one embodiment, a post fermentation gaseous substrate comprising at least one gas is received from the bioreactor and one or more gases are separated from one or more other gases. In one embodiment the post fermentation gaseous substrate comprises $H_2$. More preferably, the gas separation is effected by a Pressure Swing Adsorption (PSA) module.

Preferably, the substrate comprising CO and/or $H_2$ is received from a pressure swing adsorption module.

Preferably, the pressure swing adsorption module is used to recover hydrogen from a gas stream received from the SR or WGS step. In alternative embodiments the PSA is used to recover hydrogen from the bioreactor.

Preferably, the substrate comprising CO further comprises hydrogen and said hydrogen is recovered from the substrate.

Preferably, hydrogen recovered from the substrate is recycled to the pressure swing adsorption module.

Preferably, the hydrocarbon produced is ethanol or propanol or butanol.

Preferably, the hydrocarbon produced is reused in a SR process.

Preferably, the hydrocarbon is passed through a preformer prior to being reused in the steam reforming process. Passing through a preformer partially completes the steam reforming step of the steam reforming process which can increase the efficiency of hydrogen production and reduce the required capacity of the steam reforming furnace.

Preferably, the hydrocarbon produced is a diol, more preferably 2,3-butanediol.

Preferably, the hydrocarbon produced is butyrate, propionate, caproate, propylene, butadiene, iso-butylene, or ethylene.

Preferably the hydrocarbon produced is gasoline (about 8 carbon), jet fuel (about 12 carbon) or diesel (about 12 carbon).

Preferably, the hydrocarbon is 2,3-butanediol is used for gasoline blending.

Preferably, biomass is collected from the bioreactor and undergoes anaerobic digestion to produce a biomass product, preferably methane.

Preferably, the biomass product is used as a reactant for the steam reforming step.

Preferably, the biomass product is used to produce supplemental heat to drive one or more reactions defined herein.

In a third aspect there is provided a system for the production of a hydrocarbon product, the system comprising;
 i. a bioreactor containing a culture of one or more microorganisms adapted to produce the hydrocarbon product by fermentation of a substrate comprising CO and/or $H_2$;
wherein the substrate comprising CO and/or $H_2$ is received from a pre-forming system comprising at least one of;
 ii. a steam reforming module adapted to carry out a process generally defined by the equation: $CH_4+H_2O \rightarrow CO+3H_2$; and/or
 iii. a water-gas shift module adapted to carry out a process generally defined by the equation: $CO+H_2O \rightarrow H_2+CO_2$
wherein the pre-forming system is for treating and/or providing a substrate comprising CO for the bioreactor Preferably, the bioreactor is adapted to receive the CO and/or $H_2$ containing substrate from a water-gas shift module, wherein the water-gas shift module is adapted to carry out a water-gas shift step defined generally by the equation: $CO+H_2O \rightarrow H_2+CO_2$. More preferably, the CO and/or $H_2$ containing substrate is received from the steam reforming module, then passed to the water-gas shift module and then to the bioreactor.

Preferably, the bioreactor is adapted to receive the CO and/or $H_2$ containing substrate from a pressure swing adsorption (PSA) module.

Preferably, the PSA module receives the CO and/or $H_2$ containing substrate from the steam reforming module.

Preferably, the substrate from the steam reforming module or the water-gas shift module further comprises CO and $H_2$ and the PSA module is adapted to recover hydrogen from the substrate.

Preferably, a gas separation module adapted to separate one or more gases from one or more other gases is adapted to receive a post-fermentation substrate from the bioreactor.

Preferably, a PSA module is adapted to receive the post-fermentation substrate and recover one or more gases, preferably $H_2$, from the substrate.

Preferably, the post-fermentation substrate contains CO and the bioreactor is adapted to receive the substrate to produce a hydrocarbon product by fermentation.

Preferably, the steam reforming module is adapted to receive an amount of the hydrocarbon produced by the bioreactor.

Preferably, the steam reforming module is adapted to receive a reactant substrate comprising one or more reactants selected from the group containing methane, ethanol and butanol.

Preferably, the reactant substrate is received from a preformer module.

Preferably, a digestion module is adapted to receive biomass from the bioreactor and produce a biomass product, preferably methane.

Preferably, the steam reforming module is adapted to receive the biomass product for use as a reactant for the steam reforming process.

Preferably, the digestion module is adapted to produce supplemental heat to be supplied to one or more other modules defined herein.

According to a further embodiment the invention provides hydrogen produced by steam reforming wherein the hydrogen is received from a bioreactor containing a culture of one or more micro-organisms.

According to a fourth aspect the invention provides a method of producing a hydrocarbon product, the method including;
  i. providing a substrate comprising CO and/or $H_2$ to a bioreactor containing a culture of one or more microorganisms;
  ii. fermenting the culture in the bioreactor to produce one or more hydrocarbon products;
wherein the substrate comprising CO is received from a refinery process, said refinery process being selected from the group comprising;
  a) fluid catalytic cracking;
  b) continuous catalytic regeneration reforming;
  c) gasification of a refinery feedstock; or
  d) fluid coking.

In one embodiment there is provided a fluid catalytic cracking (FCC) process whereby a refinery feedstock is cracked in the presence of a catalyst, and wherein coke build-up on the spent catalyst is combusted to produce a CO containing gaseous substrate that is passed to the bioreactor of step (i). Preferably the FCC process is for treating and/or providing a substrate comprising CO for a bioreactor.

In one embodiment there is provided a continuous catalytic regeneration (CCR) reforming process whereby a refinery feedstock, preferably naphtha, is cracked in the presence of a catalyst, and wherein coke build-up on the spent catalyst is combusted to produce a CO containing gaseous substrate that is passed to the bioreactor of step (i). Preferably the CCR process is for treating and/or providing a substrate comprising CO for a bioreactor In one embodiment, the refinery process is fluid coking, the fluid coking process comprising;
  a) cracking a refinery feedstock, preferably vacuum gas oil, in a reactor containing hot coke at approximately 625 to 675° C. which produces cold coke at approximately 500-550° C.
  b) continuously removing the cold coke from the reactor and passing said cold coke to a gasification module which heats the cold coke to produce hot coke for return to the reactor, wherein a CO containing gaseous substrate is produced as a by-product, the CO containing gaseous substrate being for use as at least a part of the feedstock fermentation.

Preferably the CO containing gaseous substrate from the fluid coking process is passed to the bioreactor of step (i).

Preferably the gasification module heats the cold coke in the presence of air. In certain embodiments the gasification module heats the cold coke in the presence of a gaseous composition in which oxygen is enriched to a level greater than approximately 21%.

In one embodiment, the refinery process includes gasification such as gasification of a refinery feedstock (preferably a heavy residual feedstock or petroleum coke (petcoke) or coal). Preferably, at least a portion of the gas produced during gasification is syngas of which at least a portion is preferably converted to substitute natural gas (SNG). Preferably, at least a portion of the SNG is used in a refinery process such as $CO_2$ reforming or exported to the utility gas supply market.

In one embodiment, a gaseous substrate output from the bioreactor is passed to a pressure swing adsorption (PSA) module.

Preferably, the PSA module is used to recover $H_2$ from the gaseous substrate output from the bioreactor.

The refinery process may include one or more steps. According to preferred embodiments, the refinery process further comprises steam reforming or $CO_2$ reforming.

The same or a separate PSA module may receive gas different elements of (or in different stages of) the refinery process. The separation may be performed to adjust any gaseous stream fed to the refinery process and/or the bioreactor.

Preferably, a gaseous substrate output from the PSA module, which comprises any one or more of $CO_2$, $CH_4$, CO or $H_2$ is reused in a refinery process, preferably the gasification of a refinery feedstock.

Preferably, the hydrocarbon produced by the bioreactor is reused in a refinery process, preferably a steam reforming or $CO_2$ reforming process.

Preferably, the hydrocarbon product is ethanol or propanol or butanol.

Preferably, the hydrocarbon product or the hydrocarbon reactant is a diol, more preferably 2,3-butanediol.

Preferably, the 2,3-butanediol is used for gasoline blending.

Preferably, the hydrocarbon produced is butyrate, propionate, caproate, propylene, butadiene, iso-butylene, or ethylene.

Preferably the hydrocarbon produced is a component of gasoline (about 8 carbon), jet fuel (about 12 carbon) or diesel (about 12 carbon).

Preferably, biomass is collected from the bioreactor and undergoes anaerobic digestion to produce a biomass product, preferably methane.

Preferably, the biomass product is cycled to a refinery process which is preferably gasification of a refinery feedstock.

Preferably, the biomass product is used to produce supplemental heat to drive one or more refinery processes; preferably the refinery process is FCC.

According to a fifth aspect, the invention provides a system for the production of a hydrocarbon product comprising:
  i) a bioreactor containing a culture of one or more microorganisms adapted to produce the hydrocarbon by fermentation of a CO and/or $H_2$ containing substrate, wherein said substrate is received from any one or more of:
    (a) a first regenerator module adapted to combust coke build-up on spent catalyst used in a fluid catalytic cracking reactor;
    (b) a second regenerator module adapted to combust coke build-up on spent catalyst used in a continuous catalytic regeneration reforming reactor;
    (c) a gasification module adapted to gasify a refinery feedstock, preferably petcoke or a heavy residual feedstock, in the presence of oxygen;
    (d) a gasification module adapted to gasify cold coke which is preferably received from a fluid coking reactor.

Note that the gasification module adapted to gasify cold coke may be different from the gasification module adapted to gasify a refinery feedstock.

Preferably, the bioreactor is adapted to pass the CO and/or $H_2$ containing substrate to a PSA module adapted to recover $H_2$ from the gaseous substrate.

Preferably, the output gas from the PSA module is cycled to a gasification module.

Preferably, the first or second regenerator module is adapted to pass a CO containing substrate to a CO boiler which in turn passes a CO containing gaseous substrate to the bioreactor.

Preferably, the CO boiler is adapted to combust CO to produce $CO_2$ and heat. Preferably, the heat is used to produce steam for other refinery processes.

Preferably, the system comprises a gasification module adapted to gasify a refinery feedstock to produce syngas which may be used as a component of the CO containing substrate that is received by the bioreactor.

Preferably, the syngas is received by a substitute natural gas (SNG) module adapted to convert the syngas to SNG. Preferably, the SNG is received by a $CO_2$ reforming module is adapted to receive SNG for use in a $CO_2$ reforming process.

Preferably, the hydrocarbon product is ethanol or propanol or butanol.

Preferably, the hydrocarbon product or the hydrocarbon reactant is a diol, more preferably 2,3-butanediol.

Preferably, the 2,3-butanediol is used for gasoline blending.

Preferably, the hydrocarbon produced is butyrate, propionate, caproate, propylene, butadiene, iso-butylene, or ethylene.

Preferably the hydrocarbon produced is a component of gasoline (about 8 carbon), jet fuel (about 12 carbon) or diesel (about 12 carbon).

As will be appreciated, any one of the aforementioned hydrocarbon products may be directly or indirectly produced i.e., further processing modules may be used to arrive at desired products.

Preferably, a digestion module is adapted to receive biomass from the bioreactor and produce a biomass product, preferably methane.

Preferably, the biomass product is cycled to the gasification module.

Preferably, the biomass product is used to produce supplemental heat to drive one or more refinery processes; preferably the refinery process is FCC.

Preferably, the digestion module is adapted to produce supplemental heat to be supplied to one or more other modules defined herein.

For the avoidance of doubt, the output of the bioreactor of any of the fourth of fifth aspects may undergo one or more processing steps before contributing to the refining process. Similarly, products of the refining process may undergo one or more processing steps before being passed to the bioreactor.

According to a sixth aspect the invention provides a method of producing a hydrocarbon product, the method including;
  i. providing one or more by products or un-reacted feedstock components from a steam cracking process to a bioreactor containing a culture of one or more microorganisms;
  ii. fermenting the culture in the bioreactor to produce one or more hydrocarbon products.

According to a seventh aspect the invention provides a method of producing a hydrocarbon product, the method including;
  i. providing a substrate stream comprising $CO_2$ and/or $H_2$ to a bioreactor containing a culture of one or more micro-organisms;
  ii. fermenting the culture in the bioreactor to produce one or more products;

wherein the substrate comprising $CO_2$ and/or $H_2$ is received from one or more steps of a steam cracking process.

In one embodiment the steam cracking process including;
  i. steam cracking of a hydrocarbon feedstock; and
  ii. one or more separation steps separating $CO_2$ and/or $H_2$ from a steam cracking product stream.

In one embodiment, a dehydrogenated hydrocarbon stream is produced in the steam cracking process. In particular embodiments, the dehydrogenated hydrocarbon stream also comprises one or more by-products and/or one or more un-reacted feedstock components. Such by-products and/or un-reacted feedstock components can be collectively or individually substantially separated from the dehydrogenated hydrocarbon stream and passed to the fermentation step.

In one embodiment, at least a portion of $H_2$ produced in the steam cracking process is substantially separated from the dehydrogenated hydrocarbon stream and passed to the fermentation step for conversion to one or more hydrocarbon products.

In one embodiment, at least a portion of $CO_2$ is substantially separated from the dehydrogenated hydrocarbon stream and passed to the fermentation step for conversion to hydrocarbon products. In particular embodiments, additional $CO_2$ is provided in the fermentation step. Additional $CO_2$ may be substantially separated from any suitable petrochemical industry waste stream and passed to the fermentation step.

In one embodiment, at least a portion of $CH_4$ is substantially separated from the dehydrogenated hydrocarbon stream and passed to a reformation step for conversion to syngas, which is passed to the fermentation step for conversion to hydrocarbon products.

In one embodiment the invention provides a method of improving overall carbon capture of a steam cracking process, the method including passing at least a portion of one or more by-products or un-reacted feedstock components from the steam cracking process to a fermentation step for conversion into one or more hydrocarbon products.

In one embodiment the hydrocarbon products produced in the fermentation step is selected from the group comprising acetate, ethanol, propanol or butanol.

In one embodiment the hydrocarbon product or the hydrocarbon reactant is a diol, more preferably 2,3-butanediol.

In one embodiment, the 2,3-butanediol is used for gasoline blending.

In one embodiment, the hydrocarbon produced is butyrate, propionate, caproate, propylene, butadiene, iso-butylene, or ethylene.

In one embodiment the hydrocarbon produced is a component of gasoline (about 8 carbon), jet fuel (about 12 carbon) or diesel (about 12 carbon).

According to an eight aspect, the invention provides a system for the production of a hydrocarbon product, the system including
  i) a steam cracking means configured to convert a hydrocarbon feedstock to a dehydrogenated hydrocarbon stream
  ii) means for separating one or more by-products and/or one or more unreacted feedstock components from the dehydrogenated hydrocarbon stream
  iii) a bioreactor configured to receive the one or more by-products and/or one or more unreacted feedstock components from the dehydrogenated hydrocarbon stream.

In particular embodiments, the system includes one or more separation modules configured to substantially separate acidic gas components such as $CO_2$ and optionally $H_2S$ from the dehydrogenated hydrocarbon stream. Upon consideration of the instant disclosure, those skilled in the art will appreciate suitable apparatus for separating acidic gas components from the dehydrogenated hydrocarbon stream.

In particular embodiments, the system includes one or more separation modules configured to substantially separate $H_2$ and optionally $CH_4$ from the dehydrogenated hydrocarbon stream. Upon consideration of the instant disclosure, those skilled in the art will appreciate suitable apparatus for separating $H_2$ and optionally $CH_4$ from the dehydrogenated hydrocarbon stream. However, by way of non limiting example, the separation module includes one or more distillation modules.

According to a ninth aspect, the invention provides a method of producing a hydrocarbon product, the method including;
  i. providing a substrate comprising CO and/or $H_2$ to a bioreactor containing a culture of one or more microorganisms;
  ii. fermenting the culture in the bioreactor to produce one or more hydrocarbon products;
wherein the substrate comprising CO is received from a Reverse Water Gas Shift (RWGS) process, the RWGS process being generally defined by the equation $H_2+CO_2\rightarrow CO+H_2O$.

In one embodiment, the invention provides a method for improving overall carbon capture of a RWGS process, the method including passing at least a portion of a post fermentation gaseous substrate comprising $CO_2$ back to the RWGS process for conversion to a gaseous substrate comprising CO.

In one embodiment the hydrocarbon product(s) produced in the fermentation step is selected from the group comprising acetate, ethanol, propanol or butanol.

In one embodiment the hydrocarbon product is a diol, more preferably 2,3-butanediol.

In one embodiment, the 2,3-butanediol is used for gasoline blending.

In one embodiment, the hydrocarbon produced is butyrate, propionate, caproate, propylene, butadiene, iso-butylene, or ethylene.

In one embodiment the hydrocarbon produced is a component of gasoline (about 8 carbon), jet fuel (about 12 carbon) or diesel (about 12 carbon).

According to a tenth aspect of the invention, there is provided a method for producing hydrocarbon product(s), the method including at least one of;
  i. a steam reforming step, being defined generally by the equation: $CH_4+H_2O\rightarrow CO+3H_2$;
  ii. a pressure swing absorption (PSA) step, wherein a PSA module is adapted to recover at least some hydrogen from the substrate, and wherein the remaining substrate comprises CO, $CO_2$ and optionally $H_2$;
  iii. a fermentation step, wherein the substrate of step (ii) is fermented in a bioreactor containing a culture of one or more microorganisms, to produce hydrocarbon product(s) and a post fermentation gaseous substrate;
  iv. a reverse water gas shift step wherein the post fermentation gaseous substrate of step (iii) goes through a reverse water gas shift reaction, being defined generally by the equation $H_2+CO_2\rightarrow CO+H_2O$; and
  v. feeding the CO of step (iv) back into the bioreactor of step (iii) for hydrocarbon production.

In one embodiment of the invention, the feedstock provided to the steam reforming step of (i) comprises methane ($CH_4$).

In certain embodiments the post fermentation gaseous substrate of step (iii) comprises $CO_2$ and/or $H_2$.

According to an eleventh aspect, the invention provides a system for the production of a hydrocarbon product, the system including;
  i. a reverse water gas shift reactor, configured to convert a gas stream comprising $H_2$ and $CO_2$ to CO;
  ii. a bioreactor containing a culture of one or more microorganisms, said bioreactor configured receive a the CO comprising substrate of (i) and ferment the CO comprising substrate to produce hydrocarbon product(s).

In particular embodiments of the any of the preceding aspects, the fermentation step includes fermenting a substrate comprising CO in a bioreactor comprising one or more microorganisms. In particular embodiments, the micro-organism is selected from *Clostridium, Moorella, Oxobacter, Peptostreptococcus, Acetobacterium, Eubacterium* or *Butyribacterium*. In one embodiment, the micro-organism is *Acetobacterium Woodii*. In another embodiment, the micro-organism is *Clostridium autoethanogenum*.

The invention also includes the parts, elements and features referred to or indicated in the specification of the application, individually or collectively, in any or all combinations of two or more of said parts, elements or features, and where specific integers are mentioned herein which have know equivalents in the art to which the invention relates, such know equivalents are deemed to be incorporated herein as if individually set forth.

FIGURES

These and other aspects of the present invention, which should be considered in all its novel aspects, will become apparent from the following description, which is given by way of example only, with reference to the accompanying figures.

Figure 1:
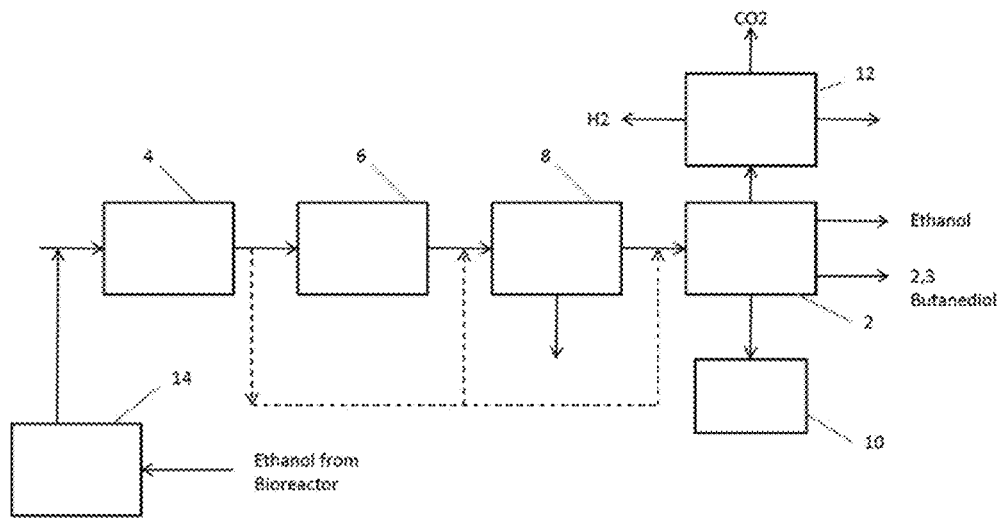
FIG. 1 shows an exemplary system and method according to one aspect of the invention.

Note that the blocks of FIGS. 1 to 11 represent both method steps and components/modules of the physical system.

DETAILED DESCRIPTION OF THE INVENTION

Definitions

Unless otherwise defined, the following terms as used throughout this specification are defined as follows:

The term "substrate comprising carbon monoxide and/or hydrogen" and like terms should be understood to include any substrate in which carbon monoxide and/or hydrogen is available to one or more strains of bacteria for growth and/or fermentation, for example.

"Gaseous substrate comprising carbon monoxide and/or hydrogen" includes any gas which contains carbon monoxide and/or hydrogen. The gaseous substrate may contain a significant proportion of CO, preferably at least about 2% to about 75% CO by volume and/or preferably about 0% to about 95% hydrogen by volume.

In the context of fermentation products, the term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. The term "acetate" includes both acetate salt alone and a mixture of molecular or free acetic acid and acetate salt, such as the mixture of acetate salt and free acetic acid present in a fermentation broth as may be described herein. The ratio of molecular acetic acid to acetate in the fermentation broth is dependent upon the pH of the system.

The term "hydrocarbon" includes any compound that includes hydrogen and carbon. The term "hydrocarbon" incorporates pure hydrocarbons comprising hydrogen and carbon, as well as impure hydrocarbons and substituted hydrocarbons. Impure hydrocarbons contain carbon and hydrogen atoms bonded to other atoms. Substituted hydrocarbons are formed by replacing at least one hydrogen atom with an atom of another element. The term "hydrocarbon" as used herein includes compounds comprising hydrogen and carbon, and optionally one or more other atoms. The one or more other atoms include, but are not limited to, oxygen, nitrogen and sulfur. Compounds encompassed by the term "hydrocarbon" as used herein include at least acetate/acetic acid; ethanol, propanol, butanol, 2,3-butanediol, butyrate, propionate, caproate, propylene, butadiene, isobutylene, ethylene, gasoline, jet fuel or diesel.

The term "bioreactor" includes a fermentation device consisting of one or more vessels and/or towers or piping arrangements, which includes a Continuous Stirred Tank Reactor (CSTR), Immobilized Cell Reactor (ICR), Trickle Bed Reactor (TBR), Bubble Column, Gas Lift Fermenter, Membrane Reactor such as a Hollow Fibre Membrane Bioreactor (HFMBR), Static Mixer, or other vessel or other device suitable for gas-liquid contact.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

"Fermentation broth" is defined as the culture medium in which fermentation occurs.

"Steam reforming process" is defined as the general process by which hydrogen is produced and recovered by the catalytic reaction of a hydrocarbon feedstock (reactant) and steam. The steam reforming process may comprise any of the following steps in any order:
  i) a steam reforming (SR) step—defined generally by the equation: $CH_4 + H_2O \rightarrow CO + 3H_2$;
  ii) a water-gas shift (WGS) step—defined generally by the equation: $CO + H_2O \rightarrow H_2 + CO_2$;
  iii) a pressure swing adsorption (PSA) step—used to recover hydrogen from the gas stream;
  iv) a gas fermentation step—where a CO and/or $H_2$ containing substrate is fermented in a bioreactor to produce a hydrocarbon product;
  v) a gas separation step—in which one or more gases are separated from one or more other gases;
  vi) a prereformer step in which hydrocarbon feedstock or product undergoes prereforming.

The steps of the above process relate generally to the modules of the system of the invention as described herein and as shown in FIG. 1.

"Refinery process" includes any one or more processes or sub-processes normally carried out in an oil refinery or similar industrial context, including, but not limited to, fluid catalytic cracking, continuous catalytic regeneration reforming, gasification, $CO_2$ reforming, steam reforming and pressure swing adsorption. While a number of particular processes that may be used in a refinery are considered in more detail herein, the invention is not limited to application to or use with such processes.

"Refinery feedstock" is defined as a product or a combination of products derived from crude oil or coal and destined for further processing other than blending in the refining industry. It is transformed into one or more components and/or finished products and may include coal, heavy fuel oil, vacuum gas oil and heavy residual feedstock.

"Heavy residual feedstock" is defined as a very high boiling point portion of a petroleum crude oil, often generated as the heaviest fraction from a crude oil distillation system.

"Cracking" refers to a process in which large, heavy, complex hydrocarbon molecules are broken down into simpler and lighter molecules in order to derive, for example, a variety of fuel products.

"Petroleum coke" (petcoke) is a carbonization product of high-boiling hydrocarbon fractions obtained in petroleum processing.

A "CO boiler" as defined herein is a module in which gas containing CO is burned and the energy produced is used to provide steam for use in a refinery as well as to comply with any applicable environmental regulatory limits on carbon monoxide emissions.

"Steam cracking process" is defined as the general process by which short chain olefins, such as ethene and/or propene are produced from a hydrocarbon feedstock, the process typically comprising steam cracking of a hydrocarbon feedstock and at least one of the following steps:
  i) compression;
  ii) water removal;
  iii) acid gas removal;
  iv) demethanization;
  v) product separation;

The "reverse water gas shift" is defined as a method of producing carbon monoxide from carbon dioxide and hydrogen. The reaction is generally defined by the following equation; $CO_2 + H_2 \rightarrow CO + H_2O$.

The reference herein to gaseous composition percentages are expressed in volume by volume (v/v) terms.

In broad terms the invention provides for a method of producing one or more hydrocarbon product(s). The invention provides for the combination of a fermentation process and an industrial process selected from the group comprising steam reforming processes, refinery processes, steam cracking processes, and reverse water gas shift processes, wherein products of one or both processes may be useful for the other. According to certain embodiments, the products transferred from one process to another comprise carbon and/or H2. Consequently by generating products from such waste, carbon capture is increased.

The Steam Reforming Process

The industrial production of hydrogen using steam reforming of suitable hydrocarbon reactants (primarily methane from natural gas) generally comprises two steps—a steam reforming step and a water-gas shift step. Where methane is referred to herein, it will be appreciated by one of skill in the art that in alternative embodiments of the invention, the steam reforming process may proceed using other suitable hydrocarbon reactants, such as ethanol, methanol, propane, gasoline, autogas and diesel fuel, all of which may have differing reactant ratios and optimal conditions.

In a typical steam reforming step, methane is reacted with steam in a molar ratio of methane:steam 3:1 in the presence of a nickel-based catalyst at a pressure of approximately 25 atm and at a temperature of approximately 700-1100° C., more preferably a temperature of approximately 800-900° C., more preferably approximately 850° C. The steam reforming reaction yields carbon monoxide and hydrogen as shown by the following equation:

$$CH_4 + H_2O \rightarrow CO + 3H_2$$

A typical output gas composition from the steam reforming step would include the following approximate composition: $H_2$—73%, $CO_2$—10%, CO—8%, $CH_4$—4%.

The second step comprises a water-gas shift reaction (WGS) where at least a portion of at least the CO produced in the steam reforming step is reacted with steam in the presence of a catalyst to produce hydrogen and carbon dioxide:

$$CO + H_2O \rightarrow H_2 + CO_2$$

The WGS step involves a high temperature shift (HTS) at a pressure of approximately 20-25 atm and a temperature of approximately 350-450° C. An aim of this step is to enrich the hydrogen content of the gas stream and to reduce the CO content. A typical gas composition from the WGS step would include the following approximate composition: $H_2$—75%, $CO_2$—16%, CO—2%, $CH_4$—3%.

The WGS step is normally followed by a Pressure Swing Adsorption (PSA) step to recover the purified hydrogen stream. The gas stream from the WGS step enters a molecular sieve system which adsorbs $CO_2$, CO, $CH_4N_2$ and $H_2O$ at high pressure. Hydrogen is able to pass through the sieve and is collected at approximately 65-90% yield (higher yield being associated with lower final $H_2$ product purity). Once saturated, the sieve is depressurised then the desorbed gases are swept out using the smallest possible quantity of hydrogen product. The extent of regeneration is a function of pressure, as a greater quantity of adsorbed species is released at lower regeneration pressures. This, in turn, leads to greater hydrogen recovery. Therefore, regeneration pressures of close to atmospheric pressure maximize hydrogen recovery. The vessel is then repressurised with hydrogen ready for the next period as adsorber. Commercial systems will typically have three or four vessels to give a smooth operation. A typical gas stream output from the PSA step would include the following: $H_2$ (approximately 7-27%), $CO_2$, CO and $CH_4$.

According to one embodiment, the present invention provides a bioreactor which receives a CO and/or $H_2$ containing substrate from one or more of the previously described processes. The bioreactor contains a culture of one or more microorganisms capable of fermenting the CO and/or $H_2$ containing substrate to produce a hydrocarbon product. Thus, steps of a steam reforming process may be used to produce or improve the composition of a gaseous substrate for a fermentation process.

According to an alternative embodiment, at least one step of a steam reforming process may be improved by providing an output of a bioreactor to an element of a steam reforming process. Preferably, the output is a gas and may enhance efficiency and/or desired total product capture (for example of $H_2$) by the steam reforming process.

Refinery Processes

Fluid Catalytic Cracking

Fluid catalytic cracking (FCC) is widely used to convert high-molecular weight hydrocarbon fractions of petroleum crude oils such as vacuum gas oil (VGO), to more valuable gasoline, olefinic gases and other products (Gary and Handwerk (2001). *Petroleum Refining: Technology and Economics* (4th ed.). CRC Press). The FCC process vaporizes and breaks the long-chain hydrocarbons into much shorter molecules by contacting the feedstock at high temperature and moderate pressure in the presence of a fluidized powdered catalyst.

A typical FCC system comprises a reactor and a regenerator. In the reactor a pre-heated high boiling point refinery feedstock (such as vacuum gas oil (VGO)) is mixed with a powdered catalyst received from the regenerator and the feedstock is vaporised and cracked into shorter chain molecules. The reactor may be operated at approximately 535° C. and 1.7 atm pressure. The cracked product vapours are separated from the catalyst and removed from the reactor to produce products such as fuel gas, light naphtha and gasoline. The catalyst that has been involved in the cracking reaction is referred to as the spent catalyst. The cracking reactions produce some carbonaceous material (referred to as coke) that forms a deposit on the catalyst and very quickly reduces the catalyst activity i.e., the catalyst may be referred to as spent. The catalyst is regenerated by burning off the deposited coke in the regenerator in the presence of oxygen (typically air). The regenerator typically operates at a temperature of about 715° C. and a pressure of about 2.38 atm. The combustion of the coke is exothermic and it produces a large amount of heat that is partially absorbed by the regenerated catalyst. The regenerated catalyst is cycled to the reactor and this provides the heat required for the vaporization of the feedstock and the endothermic cracking reactions to take place.

In combusting the coke deposited on the catalyst in the presence of oxygen, a gas containing CO is produced. The invention provides that the CO containing gas from the regenerator is received by a bioreactor in order to undergo gas fermentation. In some FCC systems, a CO boiler is used to burn the off-gases from the regenerator. A heat exchanger then uses the energy produced from burning to generate steam for various refinery operations. It is envisaged that the use of a gas fermentation step carried out in a bioreactor will reduce or eliminate the need for a CO boiler. A bioreactor has the advantage that valuable hydrocarbon products are produced from the CO rather than the gas being burned to produce the undesirable greenhouse gas $CO_2$ or directly vented.

In one embodiment, the $O_2$ content of air, normally at approximately 21%, is enriched in order to increase the level of CO in the combustion product. Similarly, the amount of CO produced during combustion can be adjusted by adjusting the amount of $O_2$ added to the process. If the amount of $O_2$ is increase, more $CO_2$ may be produced. If the amount of $O_2$ is reduced, incomplete combustion of the coke may occur resulting in a relatively higher level of CO being produced. The $O_2$ may be indirectly adjusted. For example, $N_2$ may be added to or removed from the input stream.

Continuous Catalytic Regeneration (CCR) Reforming

CCR reforming is a chemical process used to convert petroleum refinery naphtha, typically having low octane ratings, into high-octane liquid products which are components of high-octane gasoline (petrol). The process re-arranges or re-structures the hydrocarbon molecules in the naphtha feedstocks as well as breaking some of the molecules into smaller molecules. The overall effect is that the product contains hydrocarbons with more complex molecular shapes having higher octane values than the hydrocarbons in the naphtha feedstock. In so doing, the process separates hydrogen atoms from the hydrocarbon molecules and produces very significant amounts of byproduct hydrogen gas for use a number of other applications.

The naphtha feedstock is introduced to a reactor in the presence of a catalyst. CCR units are characterized by continuous regeneration of part of the catalyst in a regenerator module, and by continuous addition of the regenerated catalyst to the reactor. In a similar manner to that of FCC, the cracking reactions produce some carbonaceous material (referred to as coke) that forms a deposit on the catalyst and reduces the catalyst activity. The spent catalyst is regenerated in a regenerator by burning off the deposited coke in the regenerator in the presence of oxygen (typically air). CO gas is produced as a result of the oxidation of the coke and the invention provides that the CO containing gas is passed from the regenerator to a bioreactor to undergo gas fermentation.

Fluid Coking

Fluid coking is a continuous process in which a heated refinery feedstock, preferably vacuum gas oil or heavy residual crude, is cracked to produce lighter products such as naphtha, kerosene, heating oil, and hydrocarbon gases. The feedstock is introduced to a fluidized bed of coke particles (referred to as "hot coke") in a reactor module which are at about approximately 625 to 675° C. The feedstock is vaporised and cracked and volatile products are removed to a fractionator. The coke particles that have participated in the cracking process are referred to as "cold coke" particles and are continuously removed from the reactor to a gasification module (sometimes referred to as a burner or heater). Cold coke may be in the temperature range of approximately 500-550° C.

The coke is combusted in the presence of oxygen (preferably air) and produces a gaseous substrate containing CO. This combustion may be carried out in a CO boiler as described hereinbefore. Energy from the combustion heats the coke and this "hot coke" is then transferred back to the reactor. This process typically produces much more coke than is required for heat. Typically, fluid coke is withdrawn at the bottom of the reactor but is of low value.

Gasification

Figure 5:
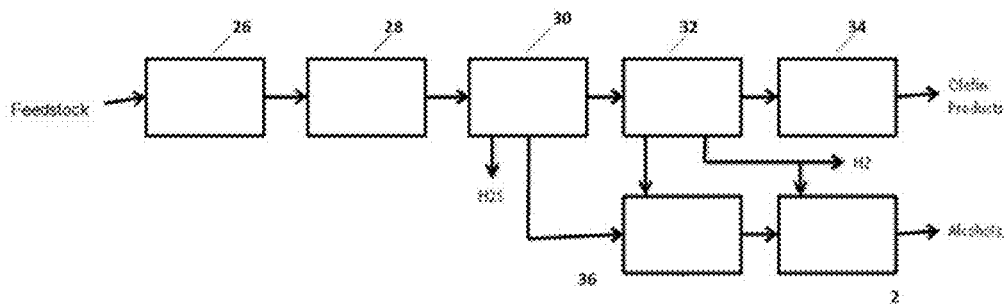
FIG. 5 shows a steam cracking system and method of one embodiment.

Refinery feedstocks such as petcoke or heavy residual feedstock or coal may be reacted in the presence of oxygen to produce a gaseous substrate, referred to as syngas, containing varying quantities of CO and $H_2$, as well as other components selected from $CO_2$, $H_2O$, $H_2S$ and $N_2$. The feedstock introduced to a gasification module and the resulting gaseous substrate may be passed to a bioreactor to undergo gas fermentation, as shown in FIG. 5.

According to one embodiment, the present invention provides a bioreactor which receives a CO and/or $H_2$ containing substrate from any one or more of the aforementioned processes. In one embodiment, a bioreactor receives a gaseous substrate from a gasification module and/or a regenerator module and/or a CO boiler.

The bioreactor contains a culture of one or more microorganisms capable of fermenting the CO and/or $H_2$ containing substrate to produce a hydrocarbon product. Thus, steps of the refinery processes defined herein may be used to produce, or improve the composition of, a gaseous substrate for a fermentation process.

Preferably, the bioreactor is adapted to receive a CO and/or $H_2$ containing substrate and contains a culture of one or more microorganisms capable of fermenting the CO and/or $H_2$ containing substrate to produce a hydrocarbon product.

According to an alternative embodiment, any of the aforementioned processes may be improved by providing an output of a bioreactor to the process. Preferably, the output is a gas and may enhance efficiency of the process and/or desired total product yield or recovery (for example of carbon or $H_2$).

The Steam Cracking Process

Steam cracking is a well known technology for production of ethylene and propylene from hydrocarbon feedstocks. The hydrocarbon feedstock, typically comprising ethane propane, or naphtha is dehydrogenated in a steam cracking furnace at elevated temperature to produce ethylene and propylene, along with a range of other species in accordance with the following:

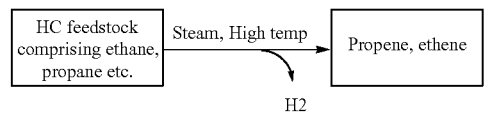

Unwanted by-products such as $H_2$ and $CH_4$ and un-reacted feedstock components such as $CO_2$ and $H_2S$ are separated through one or more separation steps. For example, the stream exiting from the steam cracker is compressed and optionally dried to remove residual water, and then sent to an acid gas removal module or modules to separate acidic gases such as $CO_2$ and $H_2S$. The ethene and propene products can be separated and purified in a number of different ways known to those skilled in the art. In an exemplary method, the product stream comprising ethene and propene can be passed through a demethanizer module, wherein volatile components such as $CH_4$ and $H_2$ are separated by distillation. In particular embodiments, the hydrogen is recovered from methane as a separate component. A downstream fractionation train then recovers ethylene and propylene from the other hydrocarbon fractions.

It has been surprisingly recognised that the $CO_2$ and $H_2$ can be diverted to a fermentation step to produce other useful liquid products, such as acetate. Converting these un-reacted components and/or by-products into useful liquid products improves the overall carbon capture efficiency of the steam cracking process. It has also been surprisingly recognised, $CH_4$ recovered from the steam cracking process can be converted to syngas in a reformation process which can be converted to liquid products including hydrocarbon products by fermentation. In particular embodiments, there is provided a method and system for improving overall carbon capture of a steam cracking process, wherein at least a portion of one or more by-products and/or un-reacted feedstock components from the stream cracking process can be converted to one or more liquid products by fermentation.

In particular embodiments, $H_2$ produced in the steam cracking process can be substantially separated from the dehydrogenated hydrocarbon stream and passed to the fermentation step for conversion to liquid products. In particular embodiments, $CO_2$ can be substantially separated from the dehydrogenated hydrocarbon stream and passed to the fermentation step for conversion to liquid products. In particular embodiments, $CH_4$ can be substantially separated from the dehydrogenated hydrocarbon stream and passed to a reformation step for conversion to syngas which can be passed to the fermentation step for conversion to liquid products.

In accordance with particular embodiments of the invention, $CO_2$ and optionally $H_2S$ separated in the acid gas removal module can be combined with $H_2$ and optionally $CH_4$ separated in the demethanization module and fermented to produce products such as acetic acid. In a particular embodiment, the $CO_2$ and $H_2$ are passed to a bioreactor comprising fermentation broth comprising one or more microorganisms, wherein the $CO_2$ and $H_2$ are converted to acetate by fermentation. In particular embodiments, additional $CO_2$ can be provided to ensure the stoichiometry for the production of acetate is approximately maintained:

$$2CO_2 + 4H_2 \rightarrow CH_3COOH + 2H_2O$$

Those skilled in the art will appreciate particular embodiments of the invention will typically be integrated into a petrochemical facility, wherein other processes producing waste $CO_2$ can be integrated, thus improving the overall carbon capture of the facility. By way of non-limiting example, the steam cracker/fermentation integrated system can be integrated with an ammonium plant or a hydrogen production plant to provide additional $CO_2$.

Figure 7:
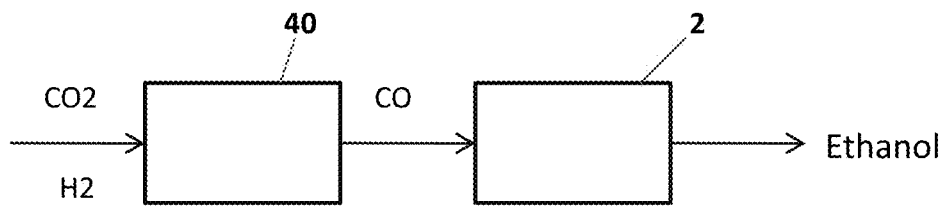
FIG. 7 shows a reverse water gas shift system and method of one embodiment.

In another embodiment of the invention, such as the embodiment depicted in FIG. 7, the $CH_4$ exiting the demethanizer module can be separated from H2 and converted to CO and H2 in a reformation process then passed to a fermentation process for conversion into liquid products, such as the processes described in WO2009010347 and U.S. 61/405,845, each of which is fully incorporated herein by reference.

Figure 8:
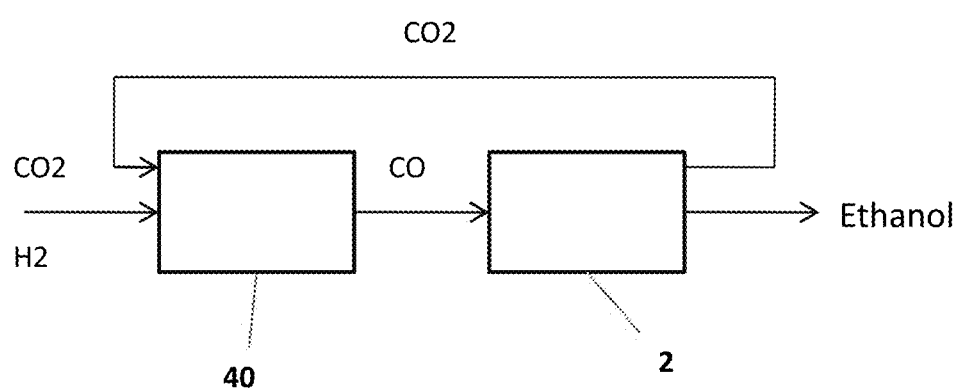
FIG. 8 shows a reverse water gas shift system and method of one embodiment.

In particular embodiments of the invention, such as the embodiment depicted in FIG. 8, wherein acetic acid is produced in the fermentation process, the acetate can be converted to vinyl acetate (VAM) by reacting it with ethylene produced in the steam cracking process. Thus, the method provides a fully integrated process for producing polymerization monomers and provides a novel route for sequestration of $CO_2$ into polymers.

CO2 and H2 Fermentation

A number of anaerobic bacteria are known to be capable of carrying out the fermentation of CO2 and H2 to alcohols, including ethanol, and acetic acid, and are suitable for use in the process of the present invention. Acetogens have the ability to convert gaseous substrates such as H2, CO2 and CO into products including acetic acid, ethanol and other fermentation products by the Wood-Ljungdahl pathway. Examples of such bacteria that are suitable for use in the invention include those of the genus *Acetobacterium*, such as strains of *Acetobacterium woodii* ((Demler, M., Weuster-Botz, "Reaction Engineering Analysis of Hydrogenotrophic Production of Acetic Acid by *Acetobacterum Woodii*", Biotechnology and Bioengineering, Vol. 108, No. 2, February 2011) and.

*Acetobacterium woodii* has been shown to produce acetate by fermentation of gaseous substrates comprising $CO_2$ and $H_2$. Buschhorn et al. demonstrated the ability of *A woodii* to produce ethanol in a glucose fermentation with a phosphate limitation.

Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Morella thermoacetica, Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp 41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Acetobacterium woodii* having the identifying characteristics of the strain deposited at the German Resource Centre for Biological Material (DSMZ) under the identifying deposit number DSM 1030.

The $CO_2$ and $H_2$ Containing Substrate

Preferably the carbon source for the fermentation can be a gaseous substrate comprising carbon dioxide in combination with hydrogen. Similarly, the gaseous substrate may be a $CO2_2$ and $H_2$ containing waste gas obtained as a by-product of an industrial process, or from some other source. The largest source of CO2 emissions globally is from the combustion of fossil fuels such as coal, oil and gas in power plants, industrial facilities and other sources.

The gaseous substrate may be a $CO_2$ and $H_2$-containing waste gas obtained as a by-product of an industrial process, or from some another source such as from automobile exhaust fumes. In certain embodiments, the industrial process is selected from the group consisting of hydrogen manufacture, ammonia manufacture, combustion of fuels, gasification of coal, and the production of limestone and cement. The gaseous substrate may be the result of blending one or more gaseous substrates to provide a blended stream. It would be understood to a skilled person that waste gas streams rich in H2 or rich in CO2 are more abundant that waste gas streams rich in both H2 and CO2. A skilled person would understand that blending one or more gas streams comprising one of the desired components of CO2 and H2 would fall within the scope of the present invention.

Hydrogen rich gas streams are produced by a variety of processes including steam reformation of hydrocarbons, and in particular steam reformation of natural gas. The partial oxidation of coal or hydrocarbons is also a source of hydrogen rich gas. Other sources of hydrogen rich gas include the electrolysis of water, by-products from electrolytic cells used to produce chlorine and from various refinery and chemical streams.

Gas streams typically rich in Carbon dioxide include exhaust gasses from combustion of a hydrocarbon, such as natural gas or oil. Carbon dioxide is also produced as a by-product from the production of ammonia, lime or phosphate and from natural carbon dioxide wells.

The Reverse Water Gas Shift

As defined above, the reverse water gas shift reaction (RWGS) is a method of producing carbon monoxide from hydrogen and carbon dioxide. In the presence of a suitable catalyst, the reaction takes place according to the following equation;

$$CO_2 + H_2 \rightarrow CO + H_2O \text{ (deltaH=+9 kcal/mole)}$$

Surprisingly we have found that we can use this reaction to make use of sources of hydrogen, particularly less desirable, impure streams containing hydrogen, with $CO_2$ to produce a CO containing gas substrate for feed to a bioreactor.

The RWGS reaction requires high temperatures. The reaction requires a hydrogen-rich and/or a carbon dioxide-rich source. A $CO_2$ and/or $H_2$ source derived from a high temperature process such as gasification would be advantageous as it would alleviate the heat requirement for the reaction.

The RWGS reaction is an efficient method for $CO_2$ separation as it requires a fraction of the power required for alternative $CO_2$ separation methods such as solid-oxide or molten carbonate electrolysis, Typically the RWGS reaction has been used to produce $H_2O$ with CO as a by product. It has been of interest in the areas of space exploration, as when used in combination with a water electrolysis device, it would be capable of providing an oxygen source.

In accordance with the present invention, the RWGS reaction is used to produce CO, with $H_2O$ being the by product. In industrial processes having $H_2$ and/or $CO_2$ waste gases, the RWGS reaction can be used to produce CO, which can then be used as a fermentation substrate in the bioreactor to produce one or more hydrocarbon product(s).

Ideal candidate streams for the reverse water gas shift reaction are low cost sources of H2 and/or CO2. Of particular interest are gas streams derived from a high temperature process such as a gasifier, as the reverse water gas shift reaction requires high temperature conditions.

Fermentation

The Bioreactor

The fermentation may be carried out in any suitable bioreactor, such as a continuous stirred tank reactor (CSTR), an immobilised cell reactor, a gas-lift reactor, a bubble column reactor (BCR), a membrane reactor, such as a Hollow Fibre Membrane Bioreactor (HFMBR) or a trickle bed reactor (TBR). Also, in some embodiments of the invention, the bioreactor may comprise a first, growth reactor in which the micro-organisms are cultured, and a second, fermentation reactor, to which fermentation broth from the growth reactor may be fed and in which most of the fermentation product (e.g. ethanol and acetate) may be produced. The bioreactor of the present invention is adapted to receive a CO and/or $H_2$ containing substrate.

The CO and/or $H_2$ Containing Substrate

The CO and/or $H_2$ containing substrate is captured or channelled from the process using any convenient method. Depending on the composition of the CO and/or $H_2$ containing substrate, it may also be desirable to treat it to remove any undesired impurities, such as dust particles before introducing it to the fermentation. For example, the substrate may be filtered or scrubbed using known methods.

The substrate comprising CO, preferably a gaseous substrate, may be obtained as a by-product of any step of the steam reforming process. Such steps include the steam reforming step, the WGS step and the PSA step as described herein.

Typically, the CO will be added to the fermentation reaction in a gaseous state. However, methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a microbubble dispersion generator (Hensirisak et. al. Scale-up of microbubble dispersion generator for aerobic fermentation; Applied Biochemistry and Biotechnology Volume 101, Number 3/October, 2002) could be used for this purpose. Where a "gas stream" is referred to herein, the term also encompasses other forms of transporting the gaseous components of that stream such as the saturated liquid method described above.

Gas Compositions

The CO-containing substrate may contain any proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 2%, may also be appropriate, particularly when $H_2$ and $CO_2$ are also present.

The presence of $H_2$ should not be detrimental to hydrocarbon product formation by fermentation. In particular embodiments, the presence of hydrogen results in an improved overall efficiency of alcohol production. For example, in particular embodiments, the substrate may comprise an approximate 2:1, or 1:1, or 1:2 ratio of $H_2$:CO. In other embodiments, the CO containing substrate comprises less than about 30% $H_2$, or less than 27% $H_2$, or less than 20% $H_2$, or less than 10% $H_2$, or lower concentrations of $H_2$, for example, less than 5%, or less than 4%, or less than 3%, or less than 2%, or less than 1%, or is substantially hydrogen free. In still other embodiments, the CO containing substrate comprises greater than 50% H2, or greater than 60% H2, or greater than 70% H2, or greater than 80% H2, or greater than 90% H2.

According to some embodiments of the invention the PSA step recovers hydrogen from the substrate received from the SR or WGS steps. In a typical embodiment, the substrate exiting the PSA step comprises about 10-35% $H_2$. The $H_2$ may pass through the bioreactor and be recovered from the substrate. In a particular embodiment of the invention, the $H_2$ is recycled to the PSA to be recovered from the substrate.

The substrate may also contain some $CO_2$ for example, such as about 1% to about 80% $CO_2$ by volume, or 1% to about 30% $CO_2$ by volume.

Fermentation

Processes for the production of ethanol and other alcohols from gaseous substrates are known. Exemplary processes include those described for example in WO2007/117157, WO2008/115080, WO2009/022925, WO2009/064200, U.S. Pat. Nos. 6,340,581, 6,136,577, 5,593,886, 5,807,722 and 5,821,111, each of which is incorporated herein by reference.

Microorganisms

In various embodiments, the fermentation is carried out using a culture of one or more strains of carboxydotrophic bacteria. In various embodiments, the carboxydotrophic bacterium is selected from *Moorella, Clostridium, Ruminococcus, Acetobacterium, Eubacterium, Butyribacterium, Oxobacter, Methanosarcina, Methanosarcina,* and *Desulfotomaculum*. A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium ragsdalei* (WO/2008/028055) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Moorella thermoacetica, Moorella thermoautotrophica, Ruminococcus productus, Acetobacterium woo-*

*dii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethanogenum* having the identifying characteristics of DSMZ deposit number DSMZ 10061. These strains have a particular tolerance to changes in substrate composition, particularly of $H_2$ and CO and as such are particularly well suited for use in combination with a steam reforming process.

Culturing of the bacteria used in the methods of the invention may be conducted using any number of processes known in the art for culturing and fermenting substrates using anaerobic bacteria. By way of example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (v) J. L. Vega, et al. (1989). Study of gaseous substrate fermentations: Carbon monoxide conversion to acetate. 1. Batch culture. Biotechnology and Bioengineering. 34. 6. 774-784; (vi) J. L. Vega, et al. (1990). Design of Bioreactors for Coal Synthesis Gas Fermentations. Resources, Conservation and Recycling. 3. 149-160; all of which are incorporated herein by reference.

Fermentation Conditions

It will be appreciated that for growth of the bacteria and CO-to-hydrocarbon fermentation to occur, in addition to the CO-containing substrate, a suitable liquid nutrient medium will need to be fed to the bioreactor. A nutrient medium will contain vitamins and minerals sufficient to permit growth of the micro-organism used. Anaerobic media suitable for the production of hydrocarbon products through fermentation using CO as the sole carbon source are known in the art. For example, suitable media are described in U.S. Pat. Nos. 5,173,429 and 5,593,886 and WO 02/08438, WO2007/115157 and WO2008/115080 referred to above.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO07/117,157 and WO08/115,080.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of hydrocarbon products. This in turn means that the retention time (defined as the liquid volume in the bioreactor divided by the input gas flow rate) can be reduced when bioreactors are maintained at elevated pressure rather than atmospheric pressure. Also, since a given CO-to-hydrocarbon conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-hydrocarbon fermentation at elevated pressures have also been described elsewhere. For example, WO 02/08438 describes gas-to-ethanol fermentations performed under pressures of 2.1 atm and 5.3 atm, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the hydrocarbon product is consumed by the culture.

Fermentation Products

Methods of the invention can be used to produce any of a variety of hydrocarbon products. This includes alcohols, acids and/or diols. More particularly, the invention may be applicable to fermentation to produce butyrate, propionate, caproate, ethanol, propanol, butanol, 2,3-butanediol, propylene, butadiene, iso-butylene, and ethylene. These and other products may be of value for a host of other processes such as the production of plastics, pharmaceuticals and agrochemicals. In a particular embodiment, the fermentation product is used to produce gasoline range hydrocarbons (about 8 carbon), diesel hydrocarbons (about 12 carbon) or jet fuel hydrocarbons (about 12 carbon).

The invention also provides that at least a portion of a hydrocarbon product produced by the fermentation is reused in the steam reforming process. This may be performed because hydrocarbons other than $CH_4$ are able to react with steam over a catalyst to produce $H_2$ and CO. In a particular embodiment, ethanol is recycled to be used as a feedstock for the steam reforming process. In a further embodiment, the hydrocarbon feedstock and/or product is passed through a preformer prior to being used in the steam reforming process. Passing through a preformer partially completes the steam reforming step of the steam reforming process which can increase the efficiency of hydrogen production and reduce the required capacity of the steam reforming furnace.

The methods of the invention can also be applied to aerobic fermentations, and to anaerobic or aerobic fermentations of other products, including but not limited to isopropanol.

Product Recovery

The products of the fermentation reaction can be recovered using known methods. Exemplary methods include those described in WO07/117,157, WO08/115,080, U.S. Pat. Nos. 6,340,581, 6,136,577, 5,593,886, 5,807,722 and 5,821,111. However, briefly and by way of example ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate, which may be produced as a by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol- and acetate-containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented microorganisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Biomass recovered from the bioreactor may undergo anaerobic digestion in a digestion.to produce a biomass product, preferably methane. This biomass product may be used as a feedstock for the steam reforming process or used to produce supplemental heat to drive one or more of the reactions defined herein.

Gas Separation/Production

The fermentation of the present invention has the advantage that it is robust to the use of substrates with impurities and differing gas concentrations. Accordingly, production of a hydrocarbon product still occurs when a wide range of gas compositions is used as a fermentation substrate. The fermentation reaction may also be used as a method to separate and/or capture particular gases (for example CO) from the substrate and to concentrate gases, for example $H_2$, for subsequent recovery. When used in conjunction with one or more other steps of the steam reforming process as defined herein, the fermentation reaction may reduce the concentration of CO in the substrate and consequently concentrate $H_2$ which enables improved $H_2$ recovery.

The gas separation module is adapted to receive a gaseous substrate from the bioreactor and to separate one or more gases from one or more other gases. The gas separation may comprise a PSA module, preferably adapted to recover hydrogen from the substrate. In a particular embodiment, the gaseous substrate from the SR step is fed directly to the bioreactor, then the resulting post-fermentation substrate passed to a gas separation module. This preferred arrangement has the advantage that gas separation is easier due to the removal of one or more impurities from the stream. The impurity may be CO. Additionally, this preferred arrangement would convert some gases to more easily separated gases, for example CO would be converted to $CO_2$.

The Steam Reforming System

Referring to FIG. 1, the bioreactor 2 may be part of a system for the production of a hydrocarbon product wherein the system comprises one or more modules selected from the group comprising:

a steam reforming (SR) module 4 adapted to produce CO according to the steam reforming step of the steam reforming process, the step being generally defined by the equation: $CH_4 + H_2O \rightarrow CO + 3H_2$;

a water-gas shift (WGS) module 6, wherein the water-gas shift module is adapted to carry out a water-gas shift step defined generally by the equation: $CO+H_2O \rightarrow H_2+CO_2$;

a pressure swing adsorption (PSA) module 8 adapted to recover hydrogen from the substrate;

a gas separation 12 module adapted to separate one or more gases from one or more other gases and adapted to receive a post-fermentation substrate from the bioreactor;

a digestion module 10 adapted to receive biomass from the bioreactor and produce a biomass product, preferably methane.

The PSA module 8 may be adapted to receive a substrate from any one or more of the SR 4, WGS 6, or PSA modules, or may be adapted to receive the post-fermentation substrate from the bioreactor 2. The PSA 8 is adapted to recover hydrogen from the substrate. The post-fermentation substrate may contain CO and/or $H_2$ and said substrate may be optionally recycled to the bioreactor to produce a hydrocarbon product. Alternatively, the hydrocarbon produced by the bioreactor 2 may be used as a feedstock for the steam reforming module. The system may optionally include a prereformer module 14 adapted to receive a hydrocarbon feedstock, which may be produced by the bioreactor 2. It will be appreciated by one of skill in the art that the modules defined herein may be operatively coupled in any suitable arrangement to effect production of a desirable product.

Omission of WGS Step

The water-gas shift (WGS) step of the process may be primarily used to reduce the level of CO in the gas stream received from the steam reforming step and to increase the concentration of $H_2$. It is envisaged in one embodiment of the invention that the WGS step may be omitted and the gas stream from the steam reforming (SR) step passed straight to the PSA step and then to the bioreactor for fermentation. Alternatively, the gas stream from the SR step may pass straight to the bioreactor for fermentation. These differing arrangements could be advantageous by reducing costs and any energy loss associated with the WGS step. Further, they may improve the fermentation process by providing a substrate having a higher CO content.

The use in embodiments of the invention of a fermentation step allows the PSA step to be less rigorous due to the possibility of channelling at least a portion of the products of the fermentation (preferably gaseous products) back to the PSA step following fermentation. More particularly, since the composition of the gas stream is altered during its passage through the bioreactor, capture of components of the stream may be more efficiently performed after fermentation thereby increasing the efficiency of the steam reforming process and/or the capture of one or more components of the stream. For instance, the PSA step can be designed with a higher regeneration pressure. While this will reduce the yield of hydrogen across the PSA step, the hydrogen can be recovered from at least a portion of the product of the fermentation. The higher regeneration pressure offers a less rigorous operating condition in the PSA step.

Carbon Capture

The steam reforming process traditionally produces a substantial quantity of $CO_2$ which is emitted to the atmosphere. However, $CO_2$ is a greenhouse gas that contributes to climate change. There is considerable pressure on industry to reduce carbon (including $CO_2$) emissions and efforts are underway to capture the carbon prior to emission. Economic incentives for reducing carbon emissions and emissions trading schemes have been established in several jurisdictions in an effort to incentivise industry to limit carbon emissions.

The present invention captures carbon from a substrate containing CO and/or $H_2$ and/or $CO_2$ and/or $CH_4$ via a fermentation process and produces a valuable hydrocarbon product ("valuable" is interpreted as being potentially useful for some purpose and not necessarily a monetary value). In the absence of the fermentation of the present invention, the CO and $CH_4$ would be likely to be burned to release energy and the resulting $CO_2$ emitted to the atmosphere. Where the energy produced is used to generate electricity, there are likely to be considerable losses in energy due to the transmission along high-voltage power lines. In contrast, the hydrocarbon product produced by the present invention may be easily transported and delivered in a usable form to industrial, commercial, residential and transportation end-users resulting in increased energy efficiency and convenience. The production of hydrocarbon products that are formed from what are effectively waste gases is an attractive proposition for industry. This is especially true for industries situated in remote locations if it is logistically feasible to transport the product long distances.

The WGS step produces $CO_2$ as a by-product. The present invention envisages the omission of the WGS step and passing of the gas stream straight to the PSA or bioreactor. Where the CO in the fermentation substrate is converted to a hydrocarbon product such as ethanol, this reduces or eliminates the emission of $CO_2$ to the atmosphere by the industrial plant.

Alternatively, the $CO_2$ may be recycled to the bioreactor, preferably in combination with a substrate comprising $H_2$. As noted hereinbefore, fermentations used in embodiments of the invention may use substrates containing $H_2$ and $CO_2$.

Refining Systems

Fluid Catalytic Cracking (FCC) System

Figure 2:
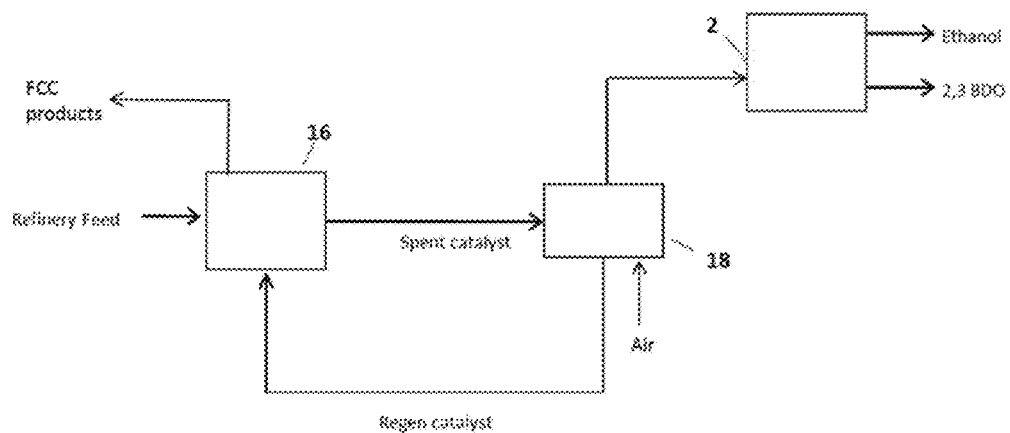
FIG. 2 shows a fluid catalytic cracking system and method of one embodiment.

FIG. 2 shows an example of a system and method incorporating both fermentation and fluid catalytic cracking. FIG. 2 shows a process of passing a refinery feed to a reactor 16. The spent catalyst is sent to the regenerator 18 for recovery of carbonaceous material (coke). The products of the catalyst regenerator 18 may be provided to a bioreactor 2 for fermentation. While not shown, one or more products of the fermentation may be circulated to the shown reactor or another processing module of a refinery.

Continuous Catalytic Regeneration (CCR) System

Figure 3:
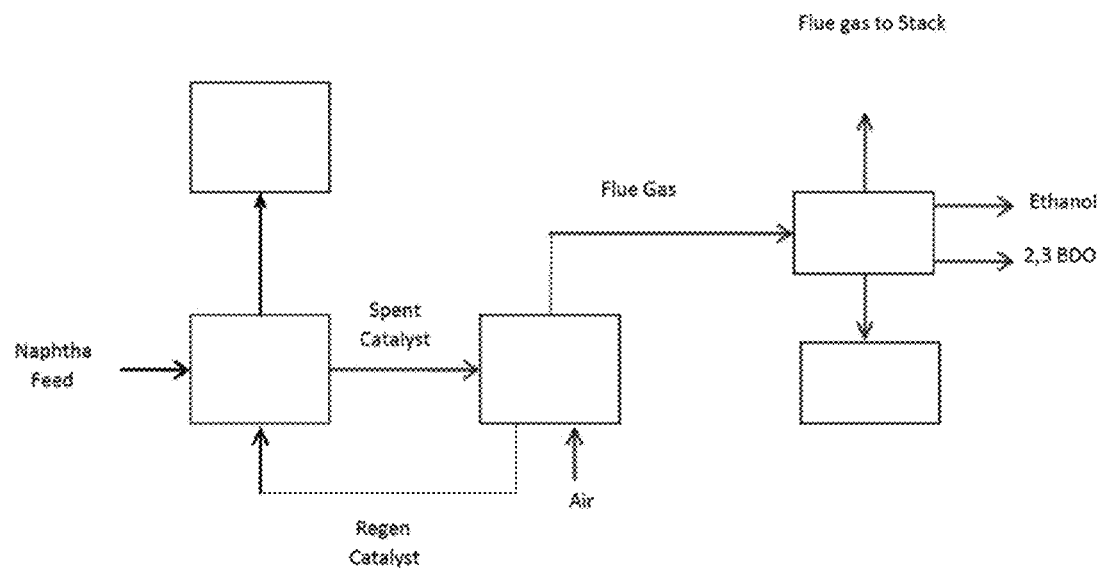
FIG. 3 shows a continuous catalytic regeneration reforming system and method of one embodiment.

FIG. 3 shows an example of a system and method incorporating both fermentation and CCR reforming. A naphtha feed is passed to a reactor 16. The spent catalyst from the reactor 16 is passed to the catalyst regenerator 18. Hydrogen can be recovered from the reactor 16 by known product recovery systems 22. Products of the catalyst regenerator 18 may be provided to a bioreactor 2 for fermentation. Biomass from the bioreactor 2 is sent to a digester 10. While not shown, one or more products of the fermentation may be circulated to the shown reactor or another processing module of a refinery.

Gasification System

Figure 4:
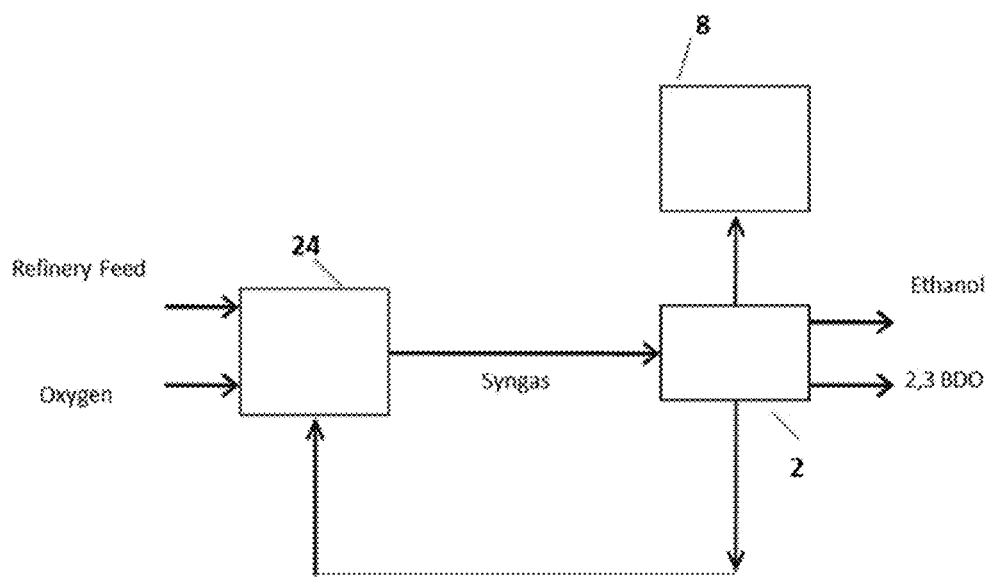
FIG. 4 shows a fluid coking system and method of one embodiment.

Referring to FIG. 4 the gasification system may also comprise a PSA 8 module adapted to receive a gaseous substrate from the gasification module 24 or the bioreactor 2. The PSA 8 is adapted to recover hydrogen from the substrate. A post-fermentation substrate from the bioreactor may contain CO and/or $H_2$ and said substrate may be optionally recycled to the gasification module 24 or the bioreactor 2. Alternatively, the hydrocarbon produced by the bioreactor 2 may be used as a feedstock for another refinery process. The output gaseous substrate from the PSA 8 may be cycled to the gasification module to improve carbon capture and/or hydrocarbon product formation/recovery.

According to a further embodiment, the invention provides that at least a portion of the syngas produced during gasification is passed to a substitute natural gas (SNG) module for conversion to SNG. SNG comprises primarily $CH_4$. The invention provides that SNG is used in addition to, or in place of, $CH_4$ from natural gas for a refinery process, preferably a $CO_2$ reforming process. The syngas produced by the gasification process may also be fed to the bioreactor in combination with syngas produced from the $CO_2$ reforming process to produce a hydrocarbon product. Any CO or $CO_2$ vented from the bioreactor may be recycled for use in the $CO_2$ reforming process or another refinery process. The remaining SNG may be exported to the utility gas market or used in other refinery processes. Among the advantages of the above described embodiment is that the gasification process, the SNG production process, the $CO_2$ reforming process and the gas fermentation process are integrated with improved efficiency, carbon capture and hydrocarbon product formation when compared to known methods.

It is envisaged that a single PSA module may be adapted to receive a gaseous substrate from more than one refinery process. Alternatively, separate modules may be provided.

The Steam Cracking System

Figure 6:
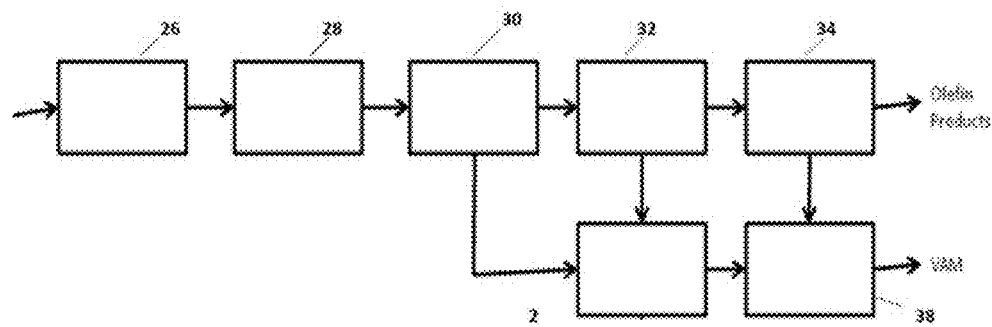
FIG. 6 shows a steam cracking system and method of an alternative embodiment.

As shown in FIGS. 5 and 6, the bioreactor may be part of a system for the production of a liquid product wherein the system includes one or more modules selected from the group comprising:
  i. a steam cracker module 26, configured to receive a hydrocarbon feedstock comprising one or more components such as ethane, propane, naptha, and dehydrogenate the one or more components at elevated temperature to give a dehydrogenated hydrocarbon stream;
  ii. a compression module 28 configured to compress the stream of dehydrogenated hydrocarbons exiting the steam cracker;
  iii. a water removal module configured to remove water from the stream of dehydrogenated hydrocarbons exiting the steam cracker, which may optionally be combined with the compression module;
  iv. an acid gas removal module 30 configured to remove acid gases, such as CO2 and H2S from the dehydrogenated hydrocarbon stream;
  v. a demethanization module 32 configured to remove H2 and CH4 from the dehydrogenated hydrocarbon stream; or
  vi. one or more further separation modules 34 configured to fractionate mixed dehydrogenated hydrocarbon products such as ethene and propene.

FIG. 5 shows a syngas production module 36 for receiving components from the acid gas removal module 30 and producing a syngas, the syngas then being passed to the bioreactor 2.

It will be appreciated by one of skill in the art that the modules defined herein may be operatively coupled in any suitable arrangement to effect production of a desirable product.

The Reverse Water Pas Shift System

In one embodiment of the present invention, there is provided a system and method for the fermentation of a substrate stream comprising CO and/or $H_2$ in a bioreactor to produce product(s). With reference to FIG. 7, a gas stream comprising $CO_2$ and $H_2$ is provided to a reverse water gas shift reactor 40. At least a portion of the $H_2$ and $CO_2$ are converted to CO by the reverse water gas shift reaction. The CO rich substrate from the reverse water gas shift reactor 40 is then passed into a bioreactor 2 containing a culture of one or more organisms. The CO is then fermented to produce product(s) including alcohol(s) and acids(s). In certain embodiments the CO is fermented to produce ethanol.

Figure 9:
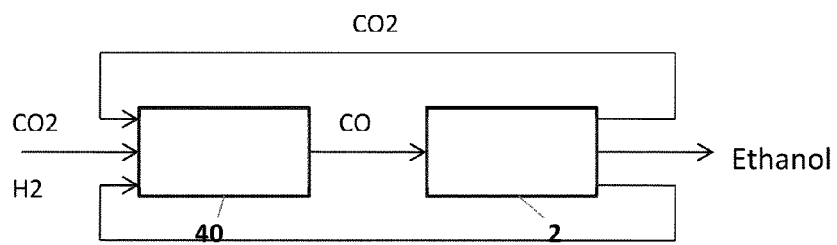
FIG. 9 shows a reverse water gas shift system and method of one embodiment.

In one embodiment of the present invention there is provided a system and method for the production of product(s) from a gas stream comprising $CO_2$ and $H_2$. One embodiment of the invention will be described with reference to the Figures. Referring to FIGS. 8 and 9, a gas stream comprising $CO_2$ and $H_2$ is supplied to a reverse water gas shift reactor 40. At least a portion of the $H_2$ and $CO_2$ introduced to the reactor is converted to CO. The resulting CO rich substrate is then passed into a bioreactor 2 comprising one or more organisms and is fermented to produce one or more product(s) and a post-fermentation stream, said post-fermentation stream comprising $CO_2$. The post-fermentation stream is then recycled back to the reverse water gas shift reactor where $H_2$ and any additional $CO_2$ required can be supplied.

Figure 10:
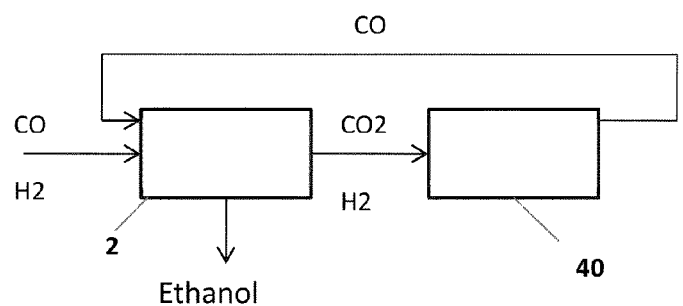
FIG. 10 shows a reverse water gas shift system and method of one embodiment.

FIG. 10 shows a third aspect of the invention, wherein a substrate comprising CO and $H_2$ is supplied to a bioreactor 2 containing one or more organisms. The substrate is fermented to produce one or more product(s) and a post-fermentation stream. According to one embodiment of the invention, the substrate comprising CO and/or $H_2$ is fermented to produce alcohols such as ethanol in accordance with the following stoichiometry;

$6CO+3H_2O->EtOH+4CO_2$; or

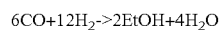

$6CO+12H_2->2EtOH+4H_2O$

As demonstrated in the above stoichiometry, the amount of $CO_2$ produced in the fermentation can be mitigated or reduced by the presence of $H_2$. In one embodiment of the invention the fermentation is conducted such that at least a portion of the $H_2$ provided in the substrate is not fermented in the bioreactor, and passes straight through, such that the post fermentation stream comprises both $CO_2$ and $H_2$. In embodiments wherein the post fermentation stream comprises $CO_2$ and $H_2$, the post fermentation stream can be passed into a reverse water gas shift reactor, for conversion to CO. Additional $H_2$ and/or $CO_2$ can be supplied to the reverse water gas shift reactor 40 from an alternative source. The resulting CO can then be returned to the bioreactor 2 for use as a substrate in the fermentation. Additional CO and or $H_2$ can be supplied to the bioreactor 2 from an alternative source if required. According to one embodiment of the invention, the fermentation reaction is adapted to consume minimal to no $H_2$, such that the majority of the $H_2$ introduced to the bioreactor 2 remains in the post-fermentation stream.

The embodiments of the previous paragraph and FIG. 10 demonstrate an embodiment of the invention wherein the initial gas source comprises CO and $H_2$. FIG. 9 shows an alternative configuration of the embodiment wherein the initial gas source is $CO_2$ and $H_2$. In this embodiment the gas stream enters the reverse water gas shift reactor first, and the CO rich substrate from the reverse water gas shift reaction is then passed into the bioreactor. $H_2$ and/or CO from an alternative source can also be supplied to the bioreactor. The fermentation produces one or more product(s) and a post-fermentation stream, said post-fermentation stream comprising $CO_2$ and preferably $H_2$ as described previously. The post-fermentation stream is then fed into the reverse water gas shift reactor. Additional $H_2$ and $CO_2$ can be supplied to the reactor.

In accordance with a fourth aspect of the present invention, a method for the fermentation of a substrate comprising CO and/or $H_2$ into liquid product, may be integrated into known processes of hydrogen production, said integration allowing for the coproduction of desired end products.

A typical hydrogen production plant comprises at least a steam reformer, a water gas shift reactor and a pressure swing adsorption unit. Typically a natural gas is supplied to the steam reformer and undergoes a reaction generally defined by the following equation: $CH_4+H_2O \rightarrow CO+3H_2$. The gas stream then undergoes a water gas shift reaction as defined by the equation: $CO+H_2O \rightarrow H_2+CO_2$. Pressure swing adsorbers are then used to recover hydrogen from the gas stream.

Figure 11:
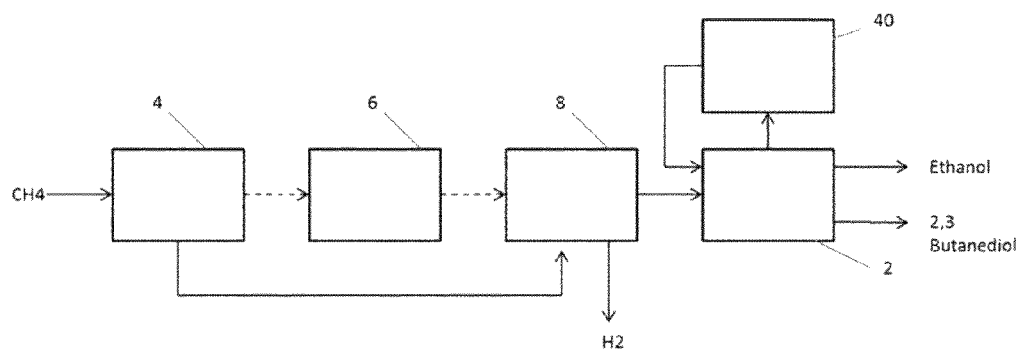
FIG. 11 shows a reverse water gas shift system and method of one embodiment.

FIG. 11 shows an embodiment of the invention, wherein the production of product(s) by microbial fermentation is integrated with a typical hydrogen production process. With reference to FIG. 11, a substrate, preferably natural gas, is passed into a steam reformer 4 where it undergoes conversion to a substrate comprising $CO_2$, CO and $H_2$. The substrate is then passed into a PSA unit 8, wherein at least a portion of the $H_2$ is recovered. The resulting substrate comprising CO, $CO_2$ and optionally $H_2$ is then passed into a bioreactor 2 containing one or more organisms. The substrate is then fermented to produce one or more product(s) and a post-fermentation stream (as previously discussed). The post-fermentation stream comprises $CO_2$ and optionally $H_2$. The post-fermentation stream is then passed into a reverse water gas shift reactor 40, wherein $CO_2$ and $H_2$ are converted to CO. The CO produced in the reverse water gas shift reactor can then by recycled back to the bioreactor for use as a substrate in the fermentation. In embodiments where all or most of the $H_2$ is recovered in the PSA's, $H_2$ can be added from an alternative source.

In certain embodiments, the above process can include an optional water gas shift reaction. In such embodiments, at least a portion of the substrate leaving the steam reformer is passed into a water gas shift reactor, wherein at least a portion of the CO undergoes a water gas shift as generally defined in the equation $CO+H_2O \rightarrow H_2+CO_2$. The substrate leaving the water gas shift reactor is then passed into the PSA, and the process continues as for the above previous embodiment.

In accordance with the invention, sources of at least one of $CO_2$ and/or $H_2$ are required. It would be understood by a skilled addressee that any suitable source of $CO_2$ and/or $H_2$ could be used for this purpose. It would also be obvious that different sources of $CO_2$ and/or $H_2$ could be combined to provide a suitable stream. It is anticipated that some source streams comprising $CO_2$ and/or $H_2$ will also comprise CO. The following sources are provided by way of example only and the invention is by no way limited to the following source streams;

- Tail gas from a hydrogen plant PSA (40-60% $CO_2$, 10-30% $H_2$, 5-15% CO);
- Coke oven gas) combined with a source of $CO_2$;
- High $CO_2$ natural gas (10-70% $CO_2$, with the balance $CH_4$, $C_2H_6$, and other hydrocarbon species) combined with a source of $H_2$;
- Biogas from natural or industrial anaerobic or aerobic digestion processes, containing 20-60% $CO_2$ with the balance $CH_4$
- $H_2$ rich gas from a catalytic reformer unit combined with a source of $CO_2$;
- Naphtha cracker offgas combined with a source of $CO_2$;
- $H_2$ rich refinery fuel gas combined with a source of $CO_2$; and
- $H_2$ purge from methanol or ammonia plant combined with a source of $CO_2$.
- $CO_2$ captured from any industrial process.
- $CO_2$ existing in flue gas from any combustion process Of particular interest are exit streams from industrial processes which comprise depleted $H_2$. A good source of hydrogen as noted above is a $H_2$ refinery, wherein $H_2$ is produced through steam reforming and a water gas shift reaction. The $H_2$ produced is then typically used for hydrogenation or other similar processes. The exit stream from the hydrogenation or other processes will contain depleted $H_2$, in other words $H_2$ with little or no further value in refinery activities. This source of depleted $H_2$ can then be converted into a useful substrate, namely CO, for fermentation into one or more product(s) in a bioreactor. Another exemplary source of Hydrogen are stranded natural gas wells. Stranded or remote natural gas wells typically comprise methane gas which cannot be used locally. According to an embodiment of the present invention, the methane from the stranded natural gas well can be converted into CO and $H_2$ by steam reforming. The CO produced by the conversion can be sent to a bioreactor for fermentation into one or more products, and the $H_2$ can be reverse water gas shifted into CO to be used in the fermentation process.

EXAMPLES

Media Preparation

| Solution A | | | |
|---|---|---|---|
| $NH_4Ac$ | 3.083 g | KCl | 0.15 g |
| $MgCl_2 \cdot 6H_2O$ | 0.61 g | NaCl | 0.12 g |
| $CaCl_2 \cdot 2H_2O$ | 0.294 g | Distilled Water | Up to 1 L |
| Component/0.1M solution (aq) Component/0.1M solution (aq) | Component/0.1M solution (aq) Quantity/ ml into 1 L media | Component/ 0.1M solution (aq) Component/0.1M solution (aq) | Component/ 0.1M solution (aq) Quantity/ml into 1 L media |
| Solution B | | | |
| $FeCl_3$ | 1 ml | $Na_2WO_4$ | 0.1 ml |
| $CoCl_2$ | 0.5 ml | $ZnCl_2$ | 0.1 ml |
| $NiCl_2$ | 0.5 ml | $Na_2MoO_4$ | 0.1 ml |
| $H_3BO_3$ | 0.1 ml | | |
| Solution C | | | |
| Biotin | 20.0 mg | Calcium D-(*)-pantothenate | 50.0 mg |
| Folic acid | 20.0 mg | Vitamin B12 | 50.0 mg |
| Pyridoxine•HCl | 10.0 mg | p-Aminobenzoic acid | 50.0 mg |
| Thiamine•HCl | 50.0 mg | Thioctic acid | 50.0 mg |
| Riboflavin | 50.0 mg | Distilled water | To 1 Litre |
| Nicotinic acid | 50.0 mg | | |
| Solution D | | | |
| $NH_4Ac$ | 3.083 g | KCl | 0.15 g |
| $MgCl_2 \cdot 6H_2O$ | 0.407 g | NaCl | 0.12 g |
| $CaCl_2 \cdot 2H_2O$ | 0.294 g | Distilled Water | Up to 1 L |
| Solution E | | | |
| $MgCl_2 \cdot 6H_2O$ | 0.407 g | KCl | 0.15 g |
| $CaCl_2 \cdot 2H_2O$ | 0.294 g | Distilled Water | Up to 1 L |
| Solution F | | | |
| Solution D | 50 ml | Solution E | 50 ml |

Bacteria:

*Clostridium autoethanogenum* was obtained from the German Resource Centre for Biological Material (DSMZ) under the identifying deposit number DSM23693.

Gaseous Substrate:

The biogas source for the gaseous substrate for this experiment was derived from methane. The methane was converted to gaseous substrate comprising CO by a steam reforming process. The steam reforming was carried out in an Inconel° 800 reactor at a temperature of around 818° C. and a temperature of around 128 psig. The reactor was loaded with a nickel-alumina catalyst and a steam to carbon ration (S/C) of 3.6 was used for the biogas reforming. Prior to the reforming process, the methane was blended with $CO_2$ to obtain a $CH_4/CO_2$ ratio of about 1.5. Steam reforming of the methane resulted in a gaseous substrate having the following composition; $H_2$ 64.7%, $N_2$ 7.69%, CO 14.1%, $CO_2$ 8.8%, $H_2S$ 0.0%.

Fermentation in Serum Bottle: Incubation was performed in two 250 ml sealed serum bottles (SB1, SB2) containing 50 ml of media. Each bottle was inoculated with 1 ml of a growing culture of *Clostridium autoethanogenum* (DSM23693). The headspace gas was then evacuated and filled to an overpressure of 25 psig with the steam reformed methane gas comprising CO. A shaking incubator was used and the reaction temperature was maintained at 37° C.

Sampling and Analytical Procedures:

Media samples were taken from the serum bottles at intervals over periods up to 44 hours. Each time the media was sampled care was taken to ensure that no gas was allowed to enter into or escape from the serum bottle. HPLC was routinely used to quantify the level of acetate and ethanol during the fermentation.

HPLC:

HPLC System Agilent 1100 Series. Mobile Phase: 0.0025N Sulfuric Acid. Flow and pressure: 0.800 mL/min. Column: Alltech IOA; Catalog #9648, 150×6.5 mm, particle size 5 µm. Temperature of column: 60° C. Detector: Refractive Index. Temperature of detector: 45° C.

Method for Sample Preparation: 400 µL of sample and 50 µL of 0.15M $ZnSO_4$ are mixed and loaded into an Eppendorf tube. The tubes are centrifuged for 3 min. at 12,000 rpm, 4° C. 200 µL of the supernatant are transferred into an HPLC vial, and 5 µL are injected into the HPLC instrument.

Pressure Measurements: Head space pressure measurements were taken from the serumbottles at intervals over periods up to 3 days. After the reaction had finished the final headspace composition was analysed by Gas Chromatography.

Gas Chromatography: Gas Chromatograph HP 5890 series II utilizing a Flame Ionization Detector. Capillary GC Column: EC1000-Alltech EC1000 30 m×0.25 mm×0.25 µm. The Gas Chromatograph was operated in Split mode with a total flow of hydrogen of 50 mL/min with 5 mL purge flow (1:10 split), a column head pressure of 10 PSI resulting in a linear velocity of 45 cm/sec. The temperature program was initiated at 60° C., held for 1 minute then ramped to 215° C. at 30° C. per minute, then held for 2 minutes. Injector temperature was 210° C. and the detector temperature was 225° C.

Example 1

1.4 liters of media solution A was aseptically and anaerobically transferred into a 2 L CSTR vessel, and continuously sparged with $N_2$. Once transferred to the fermentation vessel, the reduction state and pH of the transferred media could be measured directly via probes. The media was heated to 37° C. and stirred at 400 rpm and 1.5 ml of resazurin (2 g/L) was added. 1.0 ml of $H_3PO_4$ 85% was added to obtain a 10 mM solution. The pH was adjusted to 5.3 using $NH_4OH$. Metal ions were added according to solution B and 15 ml of solution C was added. 3 mmol cysteine-HCl was added and the pH was adjusted to pH 5.5 using $NH_4OH$.

Results

TABLE 1

| Serum bottle | Date | incubation time (days) | Acetate (g/L) | Ethanol (g/L) | Headspace (PSI) |
|---|---|---|---|---|---|
| SB1 | 08 Jun. 2011 13:45 | 0.0 | 0.88 | 0.09 | 24.0 |
| SB2 | 08 Jun. 2011 13:46 | 0.0 | 0.9 | 0.12 | 24.6 |

TABLE 1-continued

| Serum bottle | Date | incubation time (days) | Acetate (g/L) | Ethanol (g/L) | Headspace (PSI) |
|---|---|---|---|---|---|
| SB1 | 09 Jun. 2011 12:33 | 1.0 | 1.44 | 0.19 | 22.8 |
| SB2 | 09 Jun. 2011 12:33 | 1.0 | 1.57 | 0.17 | 21.3 |
| SB1 | 10 Jun. 2011 9:25 | 1.8 | 1.39 | 0.44 | 17.9 |
| SB2 | 10 Jun. 2011 9:25 | 1.8 | 1.49 | 0.45 | 19.2 |

TABLE 2

| Serumbottle | Incubation Time | Gas Composition | | | | |
|---|---|---|---|---|---|---|
| | | $CO_2$ | CO | $H_2$ | $N_2$ | H2S (ppm) |
| Start composition | 0.0 | 8.8% | 14.1% | 64.7 | 7.7% | 0 |
| SB1 | 1.8 | 15.7% | 0.0% | 75.6% | 7.4% | 13400 |
| SB2 | 1.8 | 15.6% | 0.0% | 75.7% | 7.2% | 13190 |

Table 1 shows the HPLC and headspace pressure for the two serum bottles over the duration of the fermentation. The metabolites measurements were determined immediately after inoculation and after 1.0 and 1.8 days incubation. Table 2 shows the initial gas composition in the headspace at day 0.0 and the final headspace composition at day 1.8. The results clearly show utilisation of CO. SB2 shows a decrease in CO % from 14.1% to 0.0% and an increase in $CO_2$ from 8.8% to 15.7%. Correspondingly both serum bottles show an increase in the metabolite levels between day 0.0 and day 2.9. The above results demonstrate the fermentation of CO by *C. autoethanogenum* to produce ethanol and acetate. The Hydrogen values fluctuate due to inefficient GC calibration at high $H_2$ levels but don't influence the carbon balance.

Example 2

Serum Bottles 1.9 liters of media solution A was aseptically and anaerobically transferred into a 2 L CSTR vessel, and continuously sparged with $N_2$. Once transferred to the fermentation vessel, the reduction state and pH of the transferred media could be measured directly via probes. The media was heated to 37° C. and stirred at 400 rpm and 1.5 ml of resazurin (2 g/L) was added. 1.0 ml of $H_3PO_4$ 85% was added to obtain a 10 mM solution. 2 g ammonium acetate was added and the pH was adjusted to 5.3 using $NH_4OH$.

NTA (0.15M) was added to five a final concentration of 0.03 mM. Metal ions were added according to solution B and 15 ml of solution C was added. 3 mmol cysteine was added and the pH was adjusted to pH 5.5 using $NH_4OH$.

Incubation was performed in three 250 ml sealed serum bottles (SB1, SB2 and SB3) containing 50 ml of the media. Each bottle was inoculated with 1 ml of a growing culture of *Clostridium autoethanogenum* (DSMZ number 23693). The headspace gas was then pressurised to 30 psig with a gas mixture having the following composition; $CO_2$ 5%, CO 17%, $H_2$ 70% and $N_2$ 2.5%. A shaking incubator was used and the reaction temperature was maintained at 37° C.

Results

TABLE 3

Metabolite measurements (g/L)

| Sample no. | Date | incubation time | Acetate | Ethanol | 2,3 BDO | lactic acid |
|---|---|---|---|---|---|---|
| SB1 | 22 Apr. 2011 17:35 | 0.0 | 1.01 | 0.18 | 0.03 | 0 |
| SB2 | 22 Apr. 2011 17:36 | 0.0 | 1.02 | 0.17 | 0.02 | 0 |
| SB3 | 22 Apr. 2011 18:35 | 0.0 | 1.02 | 0.16 | 0.03 | 0 |
| SB1 | 25 Apr. 2011 15:33 | 2.9 | 1.47 | 0.32 | 0.03 | 0 |
| SB2 | 25 Apr. 2011 15:33 | 2.9 | 1.73 | 0.61 | 0.03 | 0 |
| SB3 | 25 Apr. 2011 15:33 | 2.9 | 1.7 | 0.74 | 0.03 | 0 |

TABLE 4

Gas concentrations (% by volume)

| Sample Number | Incubation Time | Gas Composition | | | |
|---|---|---|---|---|---|
| | | $CO_2$ | CO | $H_2$ | $N_2$ |
| SB2 | 2.9 | 14.0% | 0.04% | 82.6% | 2.5% |
| SB3 | 2.9 | 15.11% | 0.0% | 81.3% | 2.5% |

Table 3 shows the results for the three serum bottles. The table shows the metabolites measurements immediately after inoculation and results at day 2.9. Table 4 shows the gas composition in the headspace at day 2.9. The results clearly show utilisation of CO. SB2 shows a decrease in CO % from 17% to 0.04% and an increase in $CO_2$ from 5% to 14.0%. SB3 demonstrates utilisation of all of the CO introduced to the serum bottle, and an increase in $CO_2$ from 5% to 15.11%. The gas composition in SB1 was not measured. Correspondingly all three serum bottles show an increase in the metabolite levels between day 0.0 and day 2.9. The above results demonstrate the fermentation of CO by *C autoethanogenum* to produce ethanol and acetate.

Example 4

1.4 liters of media solution A was aseptically and anaerobically transferred into a 2 L CSTR vessel, and continuously sparged with $N_2$. Once transferred to the fermentation vessel, the reduction state and pH of the transferred media could be measured directly via probes. The media was heated to 37° C. and stirred at 400 rpm and 1.5 ml of resazurin (2 g/L) was added. 0.56 ml of H3P04 85% was added to obtain a 5 mM solution. The pH of the solution was measure at 5.3. Metal ions were added according to solution B and 15 ml of solution C was added. 3 mmol cysteine-HCl was added and the pH was adjusted to pH 5.5 using $NH_4OH$. The ORP of the media solution was adjusted to −170 by the addition of $Na_2S$. The media was inoculated with 200 ml of actively growing culture of *Clostridium autoethanogenum* (DSMZ number 23693). The initial gas mixture was a real mill gas having the following composition; 44% CO, 32% $N_2$, 22% $CO_2$, 2% $H_2$. The gas mixture was switched on day 1 to a mixture having the following composition; CO 20%, $H_2$ 10%, $N_2$ 70%. On day 6 the gas mixture was transitioned to the following composition; CO 20%, $H_2$ 20%, $N_2$ 60%.

Figure 12:
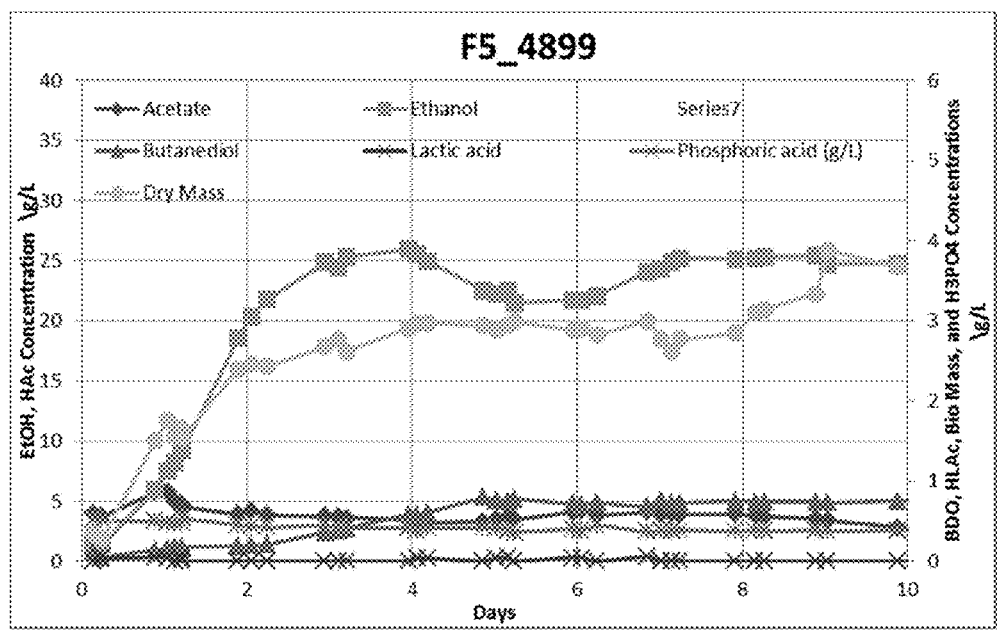
FIG. 12 shows metabolite production according to a fourth example of the present invention.

FIG. 12 shows the metabolite productivity over a 10 day period. The ethanol concentration in the bioreactor reaches approximately 25 g/L.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

Where reference has been made in the foregoing description to integers having known equivalents thereof, those integers are herein incorporated as if individually set forth.

Furthermore, titles, heading, or the like are provided to enhance the reader's comprehension of this document, and should not be read as limiting the scope of the present invention. The entire disclosures of all applications, patents and publications cited above and below, if any, are herein incorporated by reference.

The reference to any prior art in this specification is not, and should not be taken as, an acknowledgement or any form of suggestion that that prior art forms part of the common general knowledge in the field of endeavour in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

We claim as our invention:

1. A method of producing at least one product, the method comprising:
    a) passing a stream to a steam reforming reactor operated at conditions to produce a substrate comprising CO and $H_2$;
    b) passing the substrate to a bioreactor containing a culture of one or more microorganisms;
    c) fermenting the culture in the bioreactor to produce at least one product and an exit gas stream comprising $CO_2$ and $H_2$;
    d) passing the exit gas stream to a reverse water gas shift reactor operated at conditions to provide a gaseous stream comprising CO; and
    e) passing the gaseous stream comprising CO back to the bioreactor.

2. The method of claim 1 wherein the substrate from the steam reforming reactor is passed to a water gas shift reactor prior to being passed to the bioreactor.

3. The method of claim 1 further comprising passing the substrate from the steam reforming reactor to a pressure swing adsorption (PSA) module configured to recover $H_2$ from the substrate to produce an $H_2$ depleted product stream which is passed to the bioreactor.

4. The method of claim 1 further comprising passing the exit stream to a pressure swing adsorption (PSA) module wherein the PSA module recovers hydrogen from the exit gas stream prior to passing the exit gas stream to the reverse water gas shift reactor.

5. The method of claim 1 wherein the at least one product is selected from the group consisting of acetate, ethanol, propanol, butanol, 2,3-butanediol, butyrate, propionate, caproate, propylene, butadiene, isobutylene, ethylene, and mixtures thereof.

6. The method of claim 1 wherein the at least one product is a component of gasoline, or a component of jet fuel, or a component of diesel fuel.

7. The method of claim 1 wherein the one or more microorganisms is a carboxydotrophic bacterium.

8. The method of claim 7 wherein the carboxydotrophic bacterium is selected from the group consisting of *Moorella, Clostridium, Ruminococcus, Acetobacterium, Eubacterium, Butyribacterium, Oxobacter, Methanosarcina, Methanosarcina, Desulfotomaculum*, and mixtures thereof.

9. The method of claim 8 wherein the carboxydotrophic bacterium is *Clostridium autoethanogenum*.

10. The method of claim 1 where the stream is selected from the group consisting of methane, ethanol, methanol, propane, gasoline, autogas, diesel fuel and mixtures thereof.

11. The method of claim 10 where the stream is a methane stream.

* * * * *